United States Patent
Lihme et al.

(10) Patent No.: US 9,765,111 B2
(45) Date of Patent: Sep. 19, 2017

(54) SEPARATION PROCESSES FOR SOY PROTEIN

(71) Applicant: Upfront Chromatography A/S, Copenhagen Ø (DK)

(72) Inventors: Allan Otto Fog Lihme, Farum (DK); Marie Bendix Hansen, Frederiksberg (DK); Martin Pontoppidan, Kongens Lyngy (DK)

(73) Assignee: Upfront Chromatography A/S, København Ø (DK)

( * ) Notice: Subject to any disclaimer, the term of this patent is extended or adjusted under 35 U.S.C. 154(b) by 114 days.

(21) Appl. No.: 14/437,630

(22) PCT Filed: Oct. 23, 2013

(86) PCT No.: PCT/EP2013/072128
§ 371 (c)(1),
(2) Date: Apr. 22, 2015

(87) PCT Pub. No.: WO2014/064132
PCT Pub. Date: May 1, 2014

(65) Prior Publication Data
US 2015/0299275 A1   Oct. 22, 2015

Related U.S. Application Data

(60) Provisional application No. 61/717,232, filed on Oct. 23, 2012.

(30) Foreign Application Priority Data

Oct. 23, 2012   (DK) ................................ 2012 70648

(51) Int. Cl.
*C07K 14/415*   (2006.01)
*C07K 1/113*    (2006.01)
(Continued)

(52) U.S. Cl.
CPC .............. *C07K 1/22* (2013.01); *C07K 1/1136* (2013.01); *C07K 1/14* (2013.01); *C07K 14/415* (2013.01); *C08L 89/00* (2013.01)

(58) Field of Classification Search
None
See application file for complete search history.

(56) References Cited

U.S. PATENT DOCUMENTS

2001/0010930 A1 *   8/2001   Obata ..................... C12P 17/06
                                                        435/125
2010/0120107 A1 *   5/2010   Lihme ............... B01D 15/1807
                                                        435/160

FOREIGN PATENT DOCUMENTS

CH   WO 2012055986 A1 *   5/2012   ......... B01D 15/1807
WO   W09200799                1/1992
(Continued)

OTHER PUBLICATIONS

Johnson et al. (Soybeans—Chemistry, Production Processing, and Utilization, vol. 2 (2008). AOCS Press; front matter pgs., Chapter 8 on pp. 229-267, Chapter 12 on pp. 377-408, Chapter 16 on pp. 499-538, Chapter 19 on pp. 661-692. An online version of Johnson et al. is available at: http://app.knovel.com/hotlink/toc/id:kpSCP-PUV01/soybeans-chemistry-production/soybeans-chemistry-production.*

(Continued)

*Primary Examiner* — Katie L Hammer
(74) *Attorney, Agent, or Firm* — McHale & Slavin, P.A.

(57) ABSTRACT

The invention provides a process for the separation of soy protein. The process begins with an aqueous extract or solution of soy protein, which is passed through at least one expanded bed absorption (EBA) process. The EBA process comprises contacting the aqueous extract or solution of soy protein with at least one adsorbent resin, said adsorbent resin comprising at least one ligand (L1 or L2), having particular (Continued)

Figure 1:
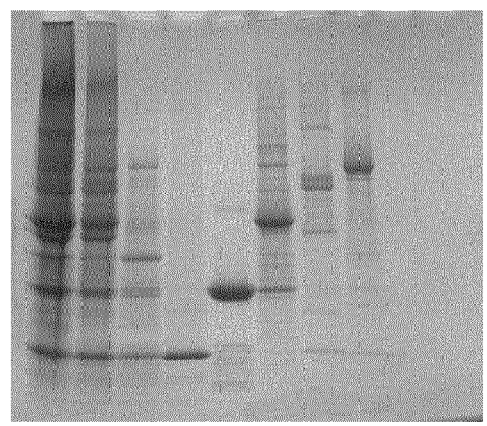

1   2   3   4   5   6   7   8 chemical structures. Proteins of interest (e.g. trypsin inhibitor (TI) protein or beta-conglycinin) are isolated by eluting them from said adsorbent resin. The invention also provides various novel protein compositions obtainable via the method of the invention.

18 Claims, 17 Drawing Sheets

(51) Int. Cl.
    *C07K 1/22*     (2006.01)
    *C07K 1/14*     (2006.01)
    *C08L 89/00*     (2006.01)

(56) References Cited

FOREIGN PATENT DOCUMENTS

| WO | W09218237 | 10/1992 |
|---|---|---|
| WO | W09808603 | 3/1998 |
| WO | WO 98/08603 | 3/1998 |
| WO | WO0158924 | 8/2001 |
| WO | WO02096215 | 12/2002 |
| WO | WO2008092450 | 8/2008 |
| WO | WO2011/082360 | 7/2011 |
| WO | WO2011082358 | 7/2011 |
| WO | WO2011082359 | 7/2011 |

OTHER PUBLICATIONS

Ge, S. et al, "Predigestion of soybean proteins with immobilized Trypsin for infant formula", Applied Biochemistry and Biotechnology, 43:3:199-209, particularly p. 202 and 204, XP002691359, (Dec. 1993).

Fields, C. et al, "Isolation of Bowman-Birk-Inhibitor from soybean extracts using novel peptide probes and high gradient magnetic separation", Food Chemistry, vol. 134, pp. 1831-1838, XP002691360, (Oct. 15, 2012).

Pusztai, A. et al, "A comprehensive scheme for the isolation of Trypsin Inhibitors and the Agglutinin from soybean seeds", Journal of Agricultural and Food Chemistry, vol. 39, pp. 862-866, XP002691361, (May 1, 1991).

Kommissarova, J., "Isolation of Kunitz trypsin inhibitors from soy whey", Nahrung, vol. 3/4, pp. 171-172, XP002691362, (Aug. 1998).

Bajpai, S. et al, "Removal and recovery of antinutritional factors from soybean flour", Food Chemistry, 89:4:497-501, XP0027770165, (Mar. 1, 2005).

Yating MA, "Deactivation of soybean agglutinin by enzyme hydrolysis and identification of active peptides from soy proteins", Iowa State University, Graduate Thesis and Dissertations, Paper 11829, (2010).

Rackis, J. et al, "Soybean trypsin inhibitors: Isolation, purification and physical properties", Archives of Biochemistry and Biophysics, 98:3:471-478, (1962).

Anderson, R. et al, "Compositional changes in trypsin inhibitors, phytic acid, saponins and isoflavones related to soybean processing", Journal of Nutrition, vol. 125/3 Supplement, pp. 581S-588S, (1995).

Heppell, L. et al, "A comparison of the antigenicity of soya-bean-based infant formulas", British Journal of Nutrition, vol. 58, pp. 393-403, (1987).

\* cited by examiner 1 2 3 4 5 6 7 8

1 2 3 4 5 6 7 8 9

1  2  3  4

5  6  7  8  9  10  11  12  13  14    15  16  17  18  19

1 2 3 4 5

1 2 3 4 5

1  2  3  4  5  6  7  8  9  10

1  2  3  4  5  6  7  8

1  2  3  4

1  2  3  4  5  6  7  8  9

1 2 3 4 5 6 7 8 9

10 11 12 13 14 15 16 17 18 19

1 2 3 4 5 6 7

8 9 10 11 12 13 14

15 16 17 18 19 20 21

22 23 24 25 26 27 28

29    30 31 32 33 34 35

36        37 38 39 40 41 42

1 2 3 4 5 6 7 8 9    10   11  12 13 14 15 16 17 18

1   2 3 4

1 2 3 4

5 6 7 8 9 10 11 12 13 14

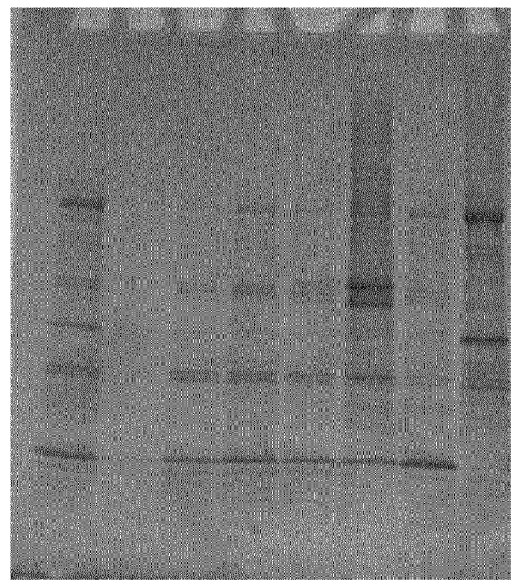
1 2 3 4 5 6 7 8
FIG: 17
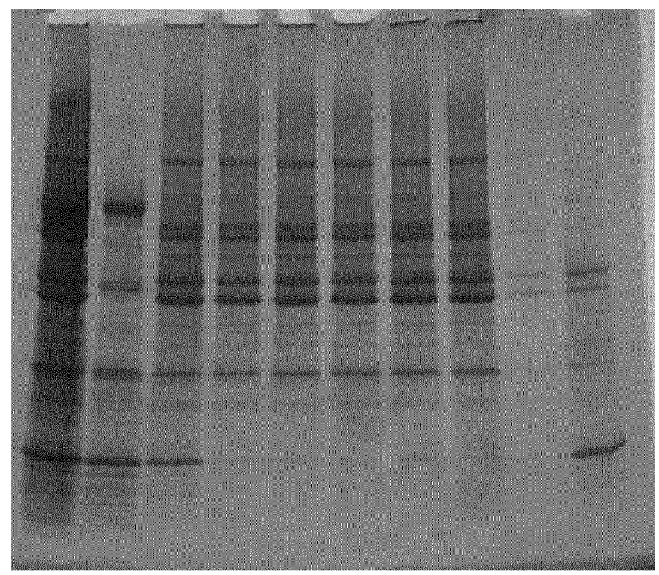
1 2 3 4 5 6 7 8 9 10
FIG. 18

10 11 12

SEPARATION PROCESSES FOR SOY PROTEIN

CROSS REFERENCE TO RELATED APPLICATIONS

This is a national stage filing in accordance with 35 U.S.C. §371 of PCT/EP2013/072128, filed Oct. 23, 2013, which claims the benefit of the priority of Denmark Patent Application No. PA 2012 70648, filed Oct. 23, 2012 and U.S. Patent Application No. 61/717,232, filed Oct. 23, 2012, the contents of each are incorporated herein by reference.

FIELD OF THE INVENTION

The present invention relates to a separation process for soy protein, as well as purified soy protein, beta-conglycinin and trypsin inhibitor protein obtained from said process.

BACKGROUND OF THE INVENTION

Soybean is an important source of protein for humans and animals, both in its unprocessed and processed form. Soybeans provide a good source of low-cost protein and have become an important world commodity because they are ubiquitous, have unique chemical composition, good nutritional value, versatile uses, and functional health benefits. Yet, less than about 5% of the soybean protein available is used for food, but this percentage is likely to grow. One of the main bodies of research in recent years has focused on studying individual storage proteins (such as glycinin, β-conglycinin and trypsin inhibitors) and relating them to industrially important functional properties and functional health benefits. In spite of this extensive research these individual proteins or enriched fractions thereof are not widely available at competitive costs.

Soy protein (i.e. protein obtained from soybeans) also contains antinutritional factors, which prevent uptake of nutrients in food. In particular, trypsin inhibitors (TIs) are proteins found among the many soy proteins which inhibits the activity of trypsin (a serine protease enzyme present in the digestive system which hydrolyses proteins). Thus, despite the beneficial functionality of these proteins in other applications, if used as part of a food or animal feed ingredient these proteins will interfere negatively with the digestive enzyme system and may lead to malnutrition and disease.

Particular efforts have therefore been made to reduce the activity of the trypsin inhibitor proteins naturally found in soy protein. A common method is simply to heat the soy protein, which denatures/destroys the trypsin inhibitor proteins. However, this technique also destroys or denatures other proteins in the soy protein, reducing their protein functions (e.g. gel-formation, fat-binding or emulsification). Proteins containing lysine are particularly heat-sensitive. Heating can also reduce the water-solubility of the soy protein.

An alternative to heating the soy protein to destroy the trypsin inhibitor (TI) protein is to separate the trypsin inhibitor (TI) protein from the remainder of the soy protein. This technique has the advantages of avoiding heat, and can also provide isolated trypsin inhibitor (TI) protein (which itself can be a useful medicinal product).

Research efforts have therefore focused on purification of soy protein to isolate the trypsin inhibitor (TI) protein contained therein. Bajpai et al. (Food Chemistry, 89 (2005), 497-501) discuss the use of immobilized metal affinity chromatography for binding trypsin inhibitor and soybean lectins.

WO2011/082358, WO2011/082359 and WO2011/082360 all concern various aspects of isolating and purifying trypsin inhibitor from soy protein.

OBJECT OF THE INVENTION

Despite the advances made to date, there remains a need for alternative processes for purification and isolation of proteins from aqueous extracts or solutions of soy protein.

SUMMARY OF THE INVENTION

It has been found by the present inventor(s) that certain ligands show selective affinity for the various proteins in soy protein.

So, in a first aspect the present invention relates to a process for the separation of soy protein, said process comprising the steps of:

i. providing an aqueous extract of soy protein or a solution of soy protein, said extract or solution of soy protein comprising at least two types of soy proteins;

ii. passing said aqueous extract or solution of soy protein through at least one expanded bed absorption process, wherein said expanded bed absorption process comprises contacting said aqueous extract or solution of soy protein with at least one adsorbent resin which selectively adsorbs at least a first type of soy protein to provide a non-bound protein fraction and a bound protein fraction, said adsorbent resin comprising:

at least one ligand (L1), said at least one ligand (L1) comprising an aromatic or heteroaromatic ring system and one or more acidic groups, or at least one ligand (L2), said at least one ligand (L2) comprising an alkylamine or alkylarylamine, wherein said alkylamine or alkylarylamine moieties in ligands (L2) comprise an amine substituted with one or more groups selected from:

a. an aryl, benzyl or heteroaryl group;

b. an alkyl group having 4-16 carbon atoms which may be straight, branched or cyclic;

or combinations thereof;

iii. isolating said first type of soy protein from said adsorbent resin, by elution of either the non-bound protein fraction or of the bound protein fraction; and iv. isolating the second type of soy protein from said adsorbent resin to provide a second soy protein composition which is depleted in said first type of soy protein.

Further details of the method, and the ligands L1 and L2 are given in the following detailed description of the invention, and the appended claims.

The invention also provides soy protein compositions, obtained by the processes of the invention. In addition, a first combined soy protein product is provided, obtained by combining the denatured TI protein obtained via the processes of the invention with the first soy protein composition depleted in TI protein obtained via processes of the invention. A second combined soy protein product is obtained by combining the denatured TI protein with the second soy protein composition depleted in TI protein.

LEGENDS TO THE FIGURES

FIGS. 1-19 illustrate SDS-PAGE gels for the examples of the invention.

DETAILED DISCLOSURE OF THE INVENTION

As set out above, the invention provides a process for the separation of soy protein, said process comprising the steps of:

i. providing an aqueous extract of soy protein or a solution of soy protein, said extract or solution of soy protein comprising at least two types of soy proteins;

ii. passing said aqueous extract or solution of soy protein through at least one expanded bed absorption process, wherein said expanded bed absorption process comprises contacting said aqueous extract or solution of soy protein with at least one adsorbent resin which selectively adsorbs at least a first type of soy protein to provide a non-bound protein fraction and a bound protein fraction, said adsorbent resin comprising:

at least one ligand (L1), said at least one ligand (L1) comprising an aromatic or heteroaromatic ring system and one or more acidic groups, or at least one ligand (L2), said at least one ligand (L2) comprising an alkylamine or alkylarylamine, wherein said alkylamine or alkylarylamine moieties in ligands (L2) comprise an amine substituted with one or more groups selected from:

a. an aryl, benzyl or heteroaryl group;

b. an alkyl group having 4-16 carbon atoms which may be straight, branched or cyclic;

or combinations thereof;

iii. isolating said first type of soy protein from said adsorbent resin, by elution of either the non-bound protein fraction or of the bound protein fraction; and iv. isolating the second type of soy protein from said adsorbent resin to provide a second soy protein composition which is depleted in said first type of soy protein.

Suitably, the steps of the process are carried out sequentially, without intervening steps.

Soybeans and Soy Protein

The soybean, *Glycine max*, is a leguminous crop grown in many parts of the world. Soybeans are of great economic importance as a source of edible oil, high-protein foods, food ingredients, and stockfeed, as well as many industrial products.

Soy protein is a general term for the protein present in soybeans. Soybean flours contain at least 50% protein and are prepared by milling soybean flakes. Due to their relatively high protein content, compositions of soy proteins are desired for a variety of applications. As well as human and animal feedstuffs, soy protein has useful properties in gel-formation, fat-binding and emulsification.

Soy proteins are not a homogeneous group. Soy proteins have been traditionally classified by their sedimentation coefficients as analyzed by ultracentrifugation into four large groups 2S (largely albumins, enzymes and trypsin inhibitors), 7S (largely β-conglycinin), 11S (largely glycinin), and 15S (largely dimers of glycinin) with peak molecular weights of approximately 25,000, 160,000, 350,000, and 600,000 respectively. A typical commercial process would yield approximately 22% 2S, 37% 7S, 31% 11S, and 11% 15S proteins as extracted by water, but these amounts may vary significantly depending on variety, crop year, handling and preceding thermal treatment.

Complex laboratory procedures have been developed to fractionate these proteins from each other. Such techniques cannot be practically applied for commercial scale production. Some of these techniques are also difficult to reproduce because small variations in the procedures significantly alter the final composition of the product.

Beta-Conglycinin Protein

Recently, there has been increased interest in obtaining purified β-conglycinin fractions, mainly to study its beneficial properties such as cholesterol-lowering and prevention of certain types of cancer. β-Conglycinin is a trimeric protein with a molecular weight of about 180 kDa. It is composed of three subunits: α' (~71 kDa), α (~67 kDa), and β (~50 kDa).

Glycinin and beta-conglycinin account for approximately 70% of the proteins in soybeans. It has been postulated that the functional properties of soy protein ingredients in food systems can be improved by modifying the ratio of these proteins. Previous attempts have been to increase the ratio of glycinin to beta-conglycinin to improve the yield and quality of tofu-type soybean gels and to improve the content of sulphur amino acids for nutritional purposes. Glycinin contains 3 to 4 times more cysteine and methionine per unit protein than beta-conglycinin. Thus it is expected that an increase in the content of glycinin and a decrease in the content of beta-conglycinin results in enhanced protein quality.

Trypsin Inhibitor Protein

Soy protein also contains a significant amount of trypsin inhibitor proteins (TI). Such inhibitors are known as serine protease inhibitors which inhibit trypsin and often inhibit other serine proteases too. Trypsin inhibitors bind in the active site of trypsin and is thereby hindering the catalytic cleavage of peptide bonds. The presence and quantification of trypsin inhibitors can be established by standard methods including competitive assays using labelled peptide substrates specific for trypsin which will be degraded at a slower rate when trypsin inhibitors are present in the analysed sample. Other more simple assays are based on gel-diffusion techniques wherein the active trypsin molecule breaks down a precipitated protein substrate and thereby creates a clarification zone the size of which being dependent on the absence or presence of trypsin inhibitors.

Trypsin, a serine protease, is responsible for cleaving peptide bonds (specifically at arginine or lysine) in the digestive system. However, if trypsin inhibitors (specifically KTI) are present, the majority of trypsin is inactivated and ingested proteins remain non-degraded. Effects of this trypsin inhibition may include gastric distress, pancreatic hyperplasia (proliferation of cells) and/or hypertrophy (enlargement of cells).

Kunitz-trypsin inhibitor (KTI, also called Kunitz soybean trypsin inhibitor) is a class of trypsin inhibitor protein whose members have approximately 170-200 amino acids, molecular weights between 20-25 kDa, and act principally against trypsin. Kunitz-trypsin proteinase inhibitors are mostly single chain polypeptides with 4 cysteines linked in two disulfide bridges, and with one reactive site located in a loop defined by a disulfide bridge. The second class of inhibitors contains 60-85 amino acids, has a range in molecular weight of 6-10 kDa, has a higher number of disulfide bonds, is relatively heat-stable, and inhibits both trypsin and chymotrypsin at independent binding sites. Bowman-Birk inhibitor (BBI) is an example of this class. The average level of protease inhibitors present in soybeans is around 1.4 percent and 0.6 percent for KTI and BBI, respectively.

Notably, these low levels make it impractical to isolate the natural protease inhibitor for clinical applications.

In one aspect, therefore, the trypsin inhibitor protein (TI) is a Kunitz-trypsin inhibitor (KTI) or a Bowman-Birk inhibitor (BBI), preferably KTI.

The Process

The process according to the invention begins from a crude aqueous extract of soy protein or solutions of soy proteins. Typically, the aqueous extract of soy protein is obtained by extracting soybeans or a soybean product (e.g. crushed soy beans, soy bean meal or defatted soybean flour) with water or a dilute acid or base. Extraction is preferably carried out for between 0.1 and 20 hours, at a temperature of between 1 and 60° C. The water may have a near-neutral pH (pH 6.5-7.5), or may be alkaline, e.g. pH 9.0-pH 12. In some instances the pH of the extraction mixture will be kept constant during extraction within a preferred range by addition of an aqueous base.

In some instances the soy protein will be a solution of soy protein derived from a crude extract by further processing such as precipitation, centrifugation and filtration including membrane filtration such as ultrafiltration, nanofiltration and microfiltration. In a preferred embodiment the soy protein solution is prepared from a protein precipitate obtained by acidification of a near neutral or alkaline soy protein extract.

A preferred solution of soy protein is soy milk. Soy milk can be made from whole soybeans or full-fat soy flour. The dry beans are soaked in water overnight or for a minimum of 3 hours or more depending on the temperature of the water. The rehydrated beans then undergo wet grinding with enough added water to give the desired solids content to the final product. The ratio of water to beans on a weight basis should be about 10:1. The resulting slurry or purée is brought to a boil in order to improve its nutritional value by heat inactivating soybean trypsin inhibitor, improve its flavor and to sterilize the product. Heating at or near the boiling point is continued for a period of time, 15-20 minutes, followed by the removal of an insoluble residue (soy pulp fiber or okara) by filtration. There is a simple yet profound difference between traditional Chinese and Japanese soy milk processing: the Chinese method boils the filtrate (soy milk) after a cold filtration, while the Japanese method boils the slurry first, followed by hot filtration of the slurry. The latter method results in a higher yield of soy milk but requires the use of an anti-foaming agent or natural defoamer during the boiling step. Bringing filtered soy milk to a boil avoids the problem of foaming. It is generally opaque, white or off-white in color, and approximately the same consistency as cow's milk. Particularly preferred is soy milk prior to heat treatment.

Other preferred soy protein solutions may be derived from the waste material soy pulp fiber (Okara) by washing, resolubilization and/or enzymatic treatment. Waste material from the production of tofu also constitutes a preferred soy protein solution.

In order to match the pH of the separation process, the aqueous extract or solution of soy protein may be pH-adjusted prior to step (ii), preferably to a pH in the range 2.0-9.0. Adjusting pH may lead to precipitation of proteins in the aqueous extract, and thus the pH-adjusted soy protein extract may be decanted, centrifuged or filtered to remove non-soluble material prior to step (ii).

The aqueous extract or solution of soy protein comprises at least two types of soy proteins—a first type and a second type.

The aqueous extract or solution of soy protein is passed through at least one separation process, which separation process comprises contacting said aqueous extract of soy protein with at least one adsorbent resin.

The adsorbent resin selectively adsorbs at least a first type of soy protein, and potentially adsorbs further soy protein. A non-bound protein fraction and a bound protein fraction are thus obtained.

The separation process is a solid phase adsorption process: expanded bed absorption (EBA).

Expanded Bed Adsorption (EBA)

Among the various industrial chromatographic separation techniques developed in recent years, Expanded Bed Adsorption (EBA) has been successfully introduced to the certain fields of biotechnology industry. EBA is a type of fluidised bed adsorption wherein the level of back-mixing is kept at a minimum. Compared with other chromatographic separation technologies, EBA offers a significant advantage because it can be used directly with non-clarified feed.

During EBA, the bed of adsorbent resin is allowed to expand inside the chromatographic column when a flow of liquid is applied. Expansion of the bed is often effected in a column having a net structure provided at each of its ends, which covers the cross-sectional area of the column, or some other perforated devices, which will not generate turbulence in the flow. See, for instance, WO-A-9218237 (Amersham Pharmacia Biotech AB, Sweden). The same effect has also been observed in a system utilising a stirred inlet flow WO-A-9200799, (UpFront Chromatography A/S).

In the expanded bed state, the distances between the adsorbent particles of the resin result in a free passage of particulate impurities in the feed stream. By contrast, traditional packed beds work as depth filters that can clog, resulting in increased back-pressure unless the feed is thoroughly clarified. Since no significant pressure builds up in an EBA column, it is possible to apply EBA without the limitations in size and flow rate normally associated with packed-bed columns. Thus, in a preferred embodiment of the present invention the adsorption process does not involve a packed bed.

An EBA process may be characterised by very limited back-mixing of the liquid inside the column as opposed to the well know turbulent fluidised beds. Back-mixing in a bed is often measured as axial dispersion ('vessel dispersion number"), see Levenspiel, "Chemical Reaction Engineering" 2nd Edition, John Wiley & Sons (1972).

The purification may be performed efficiently by applying the aqueous extract of soy protein to the adsorbent column at a linear flow rates of at least 3 cm/min, such as at least 5 cm/min, e.g. at least 8 cm/min, such as at least 10 cm/min e.g. 20 cm/min. Typically the flow rate is selected in the range of 5-50 cm/min, such as in the range of 5-15 cm/min, e.g. in the range of 10-30 cm/min, such as in the range of 25-50 cm/min.

The temperature of the soy protein solution/extract is preferably in the range of 1° C.-90° C., such as in the range of 5° C.-18° C., such as in the range of 7° C.-15° C., such as in the range of 19° C.-80° C., such as in the range of 19° C.-70° C., such as in the range of 25° C.-65° C., such as in the range of 45° C.-60° C.

When the aqueous extract or solution of soy protein is added to the adsorbent column, the ratio between the adsorbent particle present in the column and the material suspension may be optimized in order to retain a high capacity of the adsorbent column and to obtain a high purity of the protein product to be purified. In a preferred embodiment of the present invention the adsorbent present in the column relative to the aqueous extract of soy protein to be loaded on to the column are provided at a ratio of at least 1:3, such as at least 1:4, e.g. at least 1:5, such as at least 1:6, e.g. at least 1:8, such as at least 1:10, e.g. at least 1:12, such as at least 1:15, e.g. at least 1:20, such as at least 1:25, e.g. 1:30, such as 1:30 measured on a volume/volume basis.

The first type of soy protein (e.g. trypsin inhibitor (TI) protein or beta-conglycinin) is isolated from said adsorbent resin by elution of either the non-bound protein fraction or of the bound protein fraction.

The separation process may function in a number of ways, which will now be described.

The step of isolating the first type of soy protein from said resin comprises eluting trypsin inhibitor (TI) protein from said adsorbent resin. Typically the first type of soy protein fraction remains adsorbed onto the resin as the bound protein fraction, while the second type of soy protein (being the non-bound protein fraction) is eluted in a first elution (washing) step. This is followed by a second elution step which releases the first type of soy protein (being the bound protein fraction). This instance is particularly the case for ligand L2, as TI proteins are specifically bound by ligands L2.

Alternatively the second type of soy protein remains adsorbed onto the resin while the first type of soy protein is eluted from said adsorbent resin during a first elution (washing) step. In one or more subsequent elution steps the second type of soy protein is then released and isolated essentially free from the first type of soy protein.

In one aspect, essentially the entire soy protein, including the first type of soy protein, is initially adsorbed onto said adsorbent resin, and the first type of soy protein is then eluted from said adsorbent resin in a second elution step (following a first elution (washing) step to remove other non-bound substances) with or without a part of the first type of soy protein and remaining second type of soy proteins are then eluted in a third or further subsequent elution steps.

In order to obtain the purified first type of soy protein (e.g. trypsin inhibitor protein (TI)), the elution may be performed by any method conventionally described and known in the prior art. The elution of the adsorbed protein products may be performed with a solution, typically selected from the group consisting of dilute base, dilute acid, dilute buffer, dilute salt solution and water or combinations hereof. In a preferred embodiment the eluting and/or washing step is performed with a dilute solution so as to minimise the amount of salt and other unwanted substances present in the eluted product.

Preferably, the dilute solution used for elution of the first type of soy protein fraction (e.g. trypsin inhibitor protein (TI)) and/or the second type of soy protein products has a salt, buffer, acid or base concentration of less than 200 mM, preferably less than 100 mM, preferably less than 50 mM, preferably less than 30 mM, even more preferably less than 20 mM. The determination of the salt, buffer, acid or base concentration is performed directly on the eluate fraction containing the protein or proteins to be isolated without additional dilution of the eluate fraction. Common, low cost and non-toxic salt, buffers, acids and bases are applicable. Specifically preferred salts are sodium chloride, potassium chloride, calcium chloride, ammonium chloride. Specifically preferred buffers are citrate, lactate, acetate, phosphate, formate and carbonate buffers. Specifically preferred acids are citric acid, phosphoric acid, sulphuric acid, acetic acid, formic acid, hydrochloric acid. Specifically preferred are the bases sodium hydroxide (NaOH), potassium hydroxide (KOH), calcium hydroxide ($Ca(OH)_2$), ammonium hydroxide ($NH_4OH$). All of these may be combined to achieve an optimal elution procedure.

In an embodiment of the present invention elution may be performed using an eluent comprising less than 5% (v/v) of organic solvents, such as less than 3% (v/v) of organic solvent, e.g. less than 1% (v/v) organic solvent, such as 0% (v/v) of organic solvent.

Adsorbent Resin

In an embodiment of the present invention the adsorbent resin comprises at least one ligand (L1). The ligand (L1) comprises an aromatic or heteroaromatic ring system and one or more acidic groups.

Preferably the ligands (L1) comprising an aromatic or heteroaromatic ring-system and/or one or more acidic groups have a molecular weight of at the most 2000 Dalton, such as at the most 1000 Dalton such as at the most 500 Dalton.

The aromatic ring system suitably comprises a phenyl or naphthyl radical.

In an embodiment of the present invention the heteroaromatic moiety may be selected from monocyclic heteroaromatic radicals selected from thiophene, furan, pyran, pyrrole, imidazole, pyrazole, isothiazole, isoxazole, pyridine, pyrazine, pyrimidine, and pyridazine radicals; and bicyclic heteroaromatic radicals selected from indole, purine, quinoline, benzofuran, benzimidazole, benzothiazole, and benzoxazole radicals.

In a further embodiment of the present invention the acidic group is selected from a carboxylic acid group (—COOH), a sulfonic acid group (—$SO_2OH$), sulfinic acid group (—S(O)ON), phosphinic acid group (—PH(O)(OH)), phosphonic acid monoester groups (—P(O)(OH)(OR)), and phosphonic acid group (—$P(O)(OH)_2$), preferably carboxylic acid group (—COOH).

Preferably, the ligands (L1) may be derived from compounds selected from methylene-benzoic acids, hydroxy-benzoic acids, amino-benzoic acids, mercapto-benzoic acids, mercapto-nicotinic acids, mercapto-tetrazole acetic acids such as 2-amino-benzoic acid, 3-amino-benzoic acid, 4-amino-benzoic acid, 2-mercapto-benzoic acid, 3-mercapto.benzoic acid, 4-mercapto-benzoic acid, 5-mercapto-1-tetrazole acetic acid, 4-aminophthalic acid, and 5-aminoisophthalic acid.

Suitably, in ligands (L1), said one or more aromatic or heteroaromatic ring system is substituted by said one or more acidic groups. The ligands L1 may comprise more than one acidic group as well as other substituents such as basic and neutral substituents.

In an alternative embodiment of the present invention the adsorbent resin comprises at least one ligand (L2). Ligand (L2) comprises an alkylamine or alkylarylamine. The alkylamine or alkylarylamine moieties in ligands (L2) comprise an amine substituted with one or more groups selected from:
  i. an aryl, benzyl or heteroaryl group;
  ii. an alkyl group having 4-16 carbon atoms which may be straight, branched or cyclic, such as e.g., butyl, isobutyl, tert-butyl, pentyl, hexyl, heptyl, octyl, nonyl, decyl, undecyl, dodecyl, cyclopentyl, cyclohexyl or decalinyl;
or combinations thereof.

Ligands (L2) may be selected from butylamine, hexylamine, octylamine di-butylamine, pentylamine, n-pentylamine, N,N-di-methyl-1,3-di-aminopropane, 1,3-diaminopropane, 1,6-diamino hexane, 1,6-diamino hexane, 1,8-aminooctane, 1,9-di-aminononane, 1,12-aminododecane, 2-aminobenzylamine, 2-aminobenzimidazole, 2-aminoimidazole, 2,4-di-amino-6-hydroxypyrimidine, benzylamine or xylylene diamine.

Particularly preferred ligands (L2) have a C/N ratio (defined as the number of carbon atoms per nitrogen atom in the chemical formula) of at least 4, such as at least 5, such as at least 6.

In an embodiment of the present invention the concentration of the ligands (L1 or L2) is in the range of 10-990 µmol/g dry matter of adsorbent resin.

In yet an embodiment of the present invention the concentration of the ligands (L1 or L2) is in the range of 1-145 µmol/ml of hydrated, sedimented adsorbent resin.

In a further embodiment of the present invention the concentration of the ligands (L1 or L2) is in the range of 1-130 µmol/g wet, but suction-drained adsorbent resin.

Preferably the concentration of the ligands (L1 or L2) is in the range of 10-100 µmol/g wet, but suction-drained, adsorbent resin, such as in the range of 15-80 µmol/g wet, but suction-drained, adsorbent resin, such as in the range of 20-60 µmol/g wet, but suction-drained, adsorbent resin.

Besides the ligand (L1 or L2), the adsorbent resin comprises polymeric base matrix, which constitutes the bulk of the adsorbent resin, and upon which the ligands (L1 or L2) are supported.

The polymeric base matrix may be sought among certain types of natural or synthetic organic polymers, typically selected from i) natural and synthetic polysaccharides and other carbohydrate based polymers, including agar, alginate, carrageenan, guar gum, gum arabic, gum ghatti, gum tragacanth, karaya gum, locust bean gum, xanthan gum, agaroses, celluloses, pectins, mucins, dextrans, starches, heparins, chitosans, hydroxy starches, hydroxypropyl starches, carboxymethyl starches, hydroxyethyl celluloses, hydroxypropyl celluloses, and carboxymethyl celluloses; ii) synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such polymer functionally, and substituted derivatives thereof; and iii) mixtures thereof. A preferred group of polymeric base matrices are polysaccharides, such as agarose.

In an embodiment of the present invention the adsorbent resin is in the form of a particle. The adsorbent resin particle may be at least partly permeable to the protein to be isolated in order to ensure a significant binding capacity in contrast to impermeable particles that can only bind the target protein on its surface, resulting in relatively low binding capacity. The adsorbent resin particle may be of an array of different structures, compositions and shapes.

The adsorbent may further be in the form of a porous fibre or a porous membrane.

The ligands L1 or L2 may be attached to the polymer base matrix by any type of covalent bond known per se to be applicable for this purpose, either by a direct chemical reaction between the ligand and the solid phase material or by a preceding activation of the polymer base matrix or of the ligand with a suitable reagent known per se making it possible to link the matrix and the ligand.

Examples of such suitable activating reagents are epichlorohydrin, epibromohydrin, allyl-glycidylether; bis-epoxides such as butanedioldiglycidylether; halogen-substituted aliphatic compounds such as di-chloro-propanol, divinyl sulfone; carbonyldiimidazole; aldehydes such as glutaric dialdehyde; quinones; cyanogen bromide; periodates such as sodium-meta-periodate; carbodiimides; chloro-triazines such as cyanuric chloride; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides; and hydrazides. Among these, the activating reagents leaving a spacer group SP1 different from a single bond, e.g. epichlorohydrin, epibromohydrin, allyl-glycidylether; bis-epoxides; halogen-substituted aliphatic compounds; divinyl sulfone; aldehydes; quinones; cyanogen bromide; chloro-triazines; oxazolones; maleimides; pyridyl disulfides; and hydrazides, are preferred.

Especially interesting activating reagents are believed to be epoxy-compounds such as epichlorohydrin, allyl-glycidylether and butanedioldiglycidylether. In certain instances the activating reagent may even constitute a part of the functionality contributing to the binding of immunoglobulins to the polymer base matrix. e.g. in cases where divinyl sulfone is used as the activating reagent. In other cases the activating reagent is released from the matrix during reaction of the functional group with the matrix. This is the case when carbodiimidazoles and carbodiimides are used.

The above mentioned possibilities makes it relevant to define the presence of an optional spacer SP1 linking the polymer base matrix and the ligand L1 or L2. In the present context the spacer SP1 is to be considered as the part of the activating reagent which forms the link between the matrix and the ligand. Thus, the spacer SP1 corresponds to the activating reagents and the coupling reactions involved. In some cases, e.g. when using carbodiimides, the activating reagent forms an activated form of the matrix or of the ligand reagent. After coupling no parts of the activating reagent is left between the ligand and the matrix, and, thus, SP1 is simply a single bond.

In other cases the spacer SP1 is an integral part of the functional group effecting the binding characteristics, i.e. the ligand, and this will be especially significant if the spacer SP1 comprises functionally active sites or substituents such as thiols, amines, acidic groups, sulfone groups, nitro groups, hydroxy groups, nitrile groups or other groups able to interact through hydrogen bonding, electrostatic bonding or repulsion, charge transfer or the like.

In still other cases the spacer SP1 may comprise an aromatic or heteroaromatic ring which plays a significant role for the binding characteristics of the solid phase matrix. This would for example be the case if quinones or chloro-triazines where used as activation agents for the polymer base matrix or the ligand L1 or L2.

Preferably, the spacer SP1 is a single bond or a biradical derived from an activating reagent selected from epichlorohydrin, allyl-glycidylether, bis-epoxides such as butanedioldiglycidylether, halogen-substituted aliphatic compounds such as 1,3-dichloropropan-2-ol, aldehydes such as glutaric dialdehyde, divinyl sulfone, quinones, cyanogen bromide, chloro-triazines such as cyanuric chloride, 2-fluoro-1-methylpyridinium toluene-4-sulfonates, maleimides, oxazolones, and hydrazides. Preferably the spacer SP1 is selected from short chain aliphatic biradicals, e.g. of the formula —$CH_2$—$CH(OH)$—$CH_2$— (derived from epichlorohydrin), —$(CH_2)_3$—O—$CH_2$—$CH(OH)$—$CH_2$— (derived from allyl-glycidylether) or —$CH_2$—$CH(OH)$—$CH_2$—O—$(CH_2)_4$—O—$CH_2$—$CH(OH)$—$CH_2$— (derived from butanedioldiglycidylether; or a single bond.

Thus, the adsorbent resin particles may be constituted by a number of chemically derivatised porous materials having the necessary density and binding capacity to operate at the given flow rates.

The density of the adsorbent resin particle may be at least 1.3 g/mL, more preferably at least 1.5 g/mL, still more preferably at least 1.8 g/mL, even more preferably at least 2.0 g/mL, more preferably at least 2.3 g/mL, even more preferably at least 2.5 g/mL, most preferably at least 2.8 g/mL in order to enable a high productivity of the process.

In a preferred embodiment of the present invention the adsorbent resin particle has a mean particle size of at most 500 μm, particularly at most 450 μm, more particularly at most 400 μm, even more particularly at most 350 μm, even more particularly at most 300 μm, even more particularly at most 250 μm such as at most 200 μm.

The adsorbent resin particles may comprise one or more non-porous cores, within the polymeric base matrix. The polymeric base matrix acts as a means for covering and keeping multiple (or a single) core materials together. The adsorbent resin particles may be of the conglomerate type, as described in WO 92/00799, having at least two non-porous cores per particle, surrounded by a porous material. The non-porous cores in conglomerate type adsorbent resin particles are suitably of different types and sizes, e.g. a core particle consisting of two or more high density particles held together by surrounding agarose (polymeric base matrix).

The adsorbent resin particles may also be of the pellicular type having a single non-porous core per particle, surrounded by a porous material e.g. a high density stainless steel bead or a solid glass bead coated with agarose.

The non-porous core(s) constitutes typically of at most 50% of the total volume of the adsorbent resin particle, such as at most 40%, preferably at most 30%. The non-porous core (s) may be incidental distributed within the polymeric base matrix and are not necessarily located in the centre of the adsorbent resin particle.

Examples of suitable non-porous core materials are inorganic compounds, metals, heavy metals, elementary non-metals, metal oxides, non metal oxides, metal salts and metal alloys, etc. Examples of such core materials are metal silicates metal borosilicates; ceramics including titanium diboride, titanium carbide, zirconium diboride, zirconium carbide, tungsten carbide, silicon carbide, aluminum nitride, silicon nitride, titanium nitride, yttrium oxide, silicon metal powder, and molybdenum disilide; metal oxides and sulfides, including magnesium, aluminum, titanium, vanadium, chromium, zirconium, hafnium, manganese, iron, cobalt, nickel, copper and silver oxide; non-metal oxides; metal salts, including barium sulfate; metallic elements, including tungsten, zirconium, titanium, hafnium, vanadium, chromium, manganese, iron, cobalt, nickel, indium, copper, silver, gold, palladium, platinum, ruthenium, osmium, rhodium and iridium, and alloys of metallic elements, such as alloys formed between said metallic elements, e.g. stainless steel; crystalline and amorphous forms of carbon, including graphite, carbon black and charcoal. Preferred non-porous core materials are tungsten carbamide, tungsten, steel and titanium beads such as stainless steel beads.

Protein Compositions and their Production

The present invention provides routes to soy protein compositions and combined soy protein products.

A second soy protein composition depleted in the first type of soy protein is provided by isolating the second type of soy protein from the adsorbent resin. In the context of the present invention, is the second soy protein is "depleted" in the first type of soy protein, this means that the amount of first soy protein in the second soy protein is reduced by means of the method. However, in one aspect, the first type of soy protein may be completely removed from the second soy protein.

Preferably the first and second type of soy protein is separated so that the first type of soy protein contains less than 30%, such as less than 25%, such as less than 20%, such as less than 15%, such as less than 10%, such as less than 5% of the initial amount of the second type of protein when measured on a weight to weight of the proteins basis before and after the separation process.

Also preferred is that the first and second type of soy protein is separated so that the second type of soy protein contains less than 30%, such as less than 25%, such as less than 20%, such as less than 15%, such as less than 10%, such as less than 5% of the initial amount of the first type of protein when measured on a weight to weight of the proteins basis before and after the separation process.

In some instances both the first and second type of soy proteins will preferably be separated to achieve the above mentioned preferred separation levels for both type of proteins.

The second soy protein composition, depleted in the first type of soy protein, may be denatured to provide a denatured second soy protein composition. As proteins such as TI protein are not present in the first soy protein composition, denaturing may take place at a temperature lower than that required to denature TI protein. Selectivity in the denaturing process can therefore be obtained. Denaturing the second soy protein composition suitably takes place by heating to a temperature between 50° C.-100° C., such as between 50° C.-90° C., such as between 50° C.-80° C., such as between 55° C.-80° C., such as between 60° C.-80° C. Alternatively—or in combination with a heat treatment—enzymatic proteolysis may be applied to inactivate any unwanted proteins such as lipoxygenase, agglutinin and allergenic antigens.

The invention thus relates to a second soy protein composition, obtained by the process described herein.

In addition to the above, the isolated trypsin inhibitor (TI) protein may itself be denatured to provide denatured TI protein. Suitably, denaturing of the TI protein takes place by heating under pressure to a temperature between 90° C.-150° C., such as between 100° C.-130° C., such as between 100° C.-120° C. Alternatively—or in combination with a heat treatment—enzymatic proteolysis may be applied to inactivate the TI.

In additional steps, the denatured TI protein may be combined with (i) the second soy protein composition obtained herein and/or (ii) the denatured second soy protein composition obtained herein to provide various combined soy protein products.

In particular, the denatured TI protein may be combined with the second soy protein composition obtained herein (depleted in said first type of protein) to provide a first combined soy protein product.

Additionally, the denatured TI protein obtained herein may be combined with the denatured second soy protein composition obtained herein to provide a second combined soy protein product.

Furthermore, the first combined soy protein product (above), may be denatured, e.g. by heating at a temperature between 50° C.-100° C., to form a third combined soy protein product.

Various combined soy protein products of interest can therefore be obtained via the process of the invention:
  A second soy protein composition, depleted in said first type of soy protein, obtained by the process of the invention. Preferably, as the first type of soy protein is TI protein, this second soy protein composition is depleted in TI protein.
  A denatured second soy protein composition, obtained by the processes described herein.

A first combined soy protein product, obtained by the process described above.

A second combined soy protein product, obtained by the process described above.

A third combined soy protein product, obtained by denaturing the second combined soy protein product above.

Preferably, denaturing of the second combined soy protein product takes place by heating said second combined soy protein product to a temperature between 50° C.-100° C., such as between 50° C.-90° C., such as between 50° C.-80° C., such as between 55° C.-80° C., such as between 60° C.-80° C. Alternatively—or in combination with a heat treatment—enzymatic proteolysis may be applied to inactivate any unwanted proteins such as lipoxygenase, agglutinin and allergenic antigens.

EMBODIMENTS OF THE INVENTION

Embodiment 1

A process for the separation of soy protein, said process comprising the steps of:
i. providing an aqueous extract of soy protein or a solution of soy protein, said extract or solution of soy protein comprising at least two types of soy proteins;
ii. passing said aqueous extract or solution of soy protein through at least one expanded bed absorption process, wherein said expanded bed absorption process comprises contacting said aqueous extract or solution of soy protein with at least one adsorbent resin which selectively adsorbs at least a first type of soy protein to provide a non-bound protein fraction and a bound protein fraction, said adsorbent resin comprising:
at least one ligand (L1), said at least one ligand (L1) comprising an aromatic or heteroaromatic ring system and one or more acidic groups, or
at least one ligand (L2), said at least one ligand (L2) comprising an alkylamine or alkylarylamine, wherein said alkylamine or alkylarylamine moieties in ligands (L2) comprise an amine substituted with one or more groups selected from:
a. an aryl, benzyl or heteroaryl group;
b. an alkyl group having 4-16 carbon atoms which may be straight, branched or cyclic;
or combinations thereof;
iii. isolating said first type of soy protein from said adsorbent resin, by elution of either the non-bound protein fraction or of the bound protein fraction; and
iv. isolating the second type of soy protein from said adsorbent resin to provide a second soy protein composition which is depleted in said first type of soy protein.

Embodiment 2

The process according to any one of the preceding embodiments, wherein the second type of soy protein remains adsorbed onto said resin while said first type of soy protein is eluted from said adsorbent resin.

Embodiment 3

The process according to any one of the preceding embodiments, wherein first and second types of soy protein are initially both adsorbed onto said adsorbent resin, and said first type of soy protein is then eluted from said adsorbent resin.

Embodiment 4

The process according to embodiment 3, wherein eluting said first type of soy protein from said adsorbent resin occurs via an increase in pH of the eluent.

Embodiment 5

The process according to any one of the preceding embodiments, further comprising the step of denaturing the second soy protein composition to provide a denatured second soy protein composition.

Embodiment 6

The process according to embodiment 5, wherein denaturing the second soy protein composition takes place by heating to a temperature between 50° C.-100° C.

Embodiment 7

The process according to any one of the preceding embodiments, wherein the first type of protein is beta-conglycinin.

Embodiment 8

The process according to embodiment 2, wherein beta-conglycinin is eluted as the non-bound protein fraction.

Embodiment 9

The process according to embodiment 2, wherein beta-conglycinin is eluted as the bound protein fraction.

Embodiment 10

The process according to any one of embodiments 1-6, wherein the first type of protein is trypsin inhibitor (TI) protein.

Embodiment 11

The process according to embodiment 10, wherein trypsin inhibitor (TI) protein is eluted as the non-bound protein fraction.

Embodiment 12

The process according to embodiment 10, wherein trypsin inhibitor (TI) protein is eluted as the bound protein fraction.

Embodiment 13

The process according to any one of the preceding embodiments, in which the first type of protein comprises both trypsin inhibitor (TI) protein and beta-conglycinin.

Embodiment 14

The process according to any one of embodiments 10-13, further comprising the step of denaturing the isolated trypsin inhibitor (TI) protein to provide denatured TI protein, e.g. by heating to a temperature between 50 and 150° C., preferably between 75 and 120° C.

Embodiment 15

The process according to embodiment 14, further comprising the step of combining said denatured TI protein with the second soy protein composition obtained in embodiment 5 to provide a first combined soy protein product.

Embodiment 16

The process according to embodiment 14, further comprising the step of combining said denatured TI protein the denatured second soy protein composition obtained in embodiment 5 to provide a second combined soy protein product.

Embodiment 17

The process according to embodiment 15, wherein said first combined soy protein product, is denatured, e.g. by heating at a temperature between 50° C.-100° C., to form a third combined soy protein product.

Embodiment 18

The process according to any one of the preceding embodiments, wherein the ligands (L1) comprising an aromatic or heteroaromatic ring-system and/or one or more acidic groups have a molecular weight of at the most 2000 Dalton, such as at the most 1000 Dalton such as at the most 500 Dalton.

Embodiment 19

The process according to any one of the preceding embodiments, wherein the ligands (L1) comprise an aromatic ring system, preferably a phenyl or naphthyl radical.

Embodiment 20

The process according to any one of the preceding embodiments, wherein the ligands (L1) comprise a heteroaromatic ring system, which may be selected from monocyclic hetero-aromatic radicals selected from thiophene, furan, pyran, pyrrole, imidazole, pyrazole, isothiazole, isoxazole, pyridine, pyrazine, pyrimidine, and pyridazine radicals; and bicyclic heteroaromatic radicals selected from indole, purine, quinoline, benzofuran, benzimidazole, benzothiazole, and benzoxazole radicals.

Embodiment 21

The process according to any one of the preceding embodiments, wherein the ligands (L1) comprise an acidic group selected from a carboxylic acid group (—COOH), a sulfonic acid group (—SO$_2$OH), sulfinic acid group (—S(O)OH), phosphinic acid group (—PH(O)(OH)), phosphonic acid monoester groups (—P(O)(OH)(OR)), and phosphonic acid group (—P(O)(OH)$_2$), preferably carboxylic acid group (—COOH).

Embodiment 22

The process according to any one of the preceding embodiments, wherein the ligands (L1) are selected from methylene-benzoic acids, hydroxy-benzoic acids, amino-benzoic acids, mercapto-benzoic acids, mercapto-nicotinic acids, mercapto-tetrazole acetic acids such as 2-amino-benzoic acid, 3-amino-benzoic acid, 4-amino-benzoic acid, 2-mercapto-benzoic acid, 3-mercapto.benzoic acid, 4-mercapto-benzoic acid, 5-mercapto-1-tetrazole acetic acid, 4-aminophthalic acid, and 5-aminoisophthalic acid.

Embodiment 23

The process according to any one of the preceding embodiments, wherein—in the ligands (L1)—said one or more aromatic or heteroaromatic ring system is substituted by said one or more acidic groups.

Embodiment 24

The process according to any one of embodiments 1-17, wherein said alkylamine or alkylarylamine moieties in ligands (L2) comprise an amine substituted with one or more groups selected from: an alkyl group having 4-16 carbon atoms which may be straight, branched or cyclic, such as e.g. butyl, isobutyl, tert-butyl, pentyl, hexyl, heptyl, octyl, nonyl, decyl, undecyl, dodecyl, cyclopentyl, cyclohexyl or decalinyl;

Embodiment 25

The process according to embodiment 24, wherein said ligands (L2) are selected from butylamine, hexylamine, octylamine di-butylamine, pentylamine, n-pentylamine, N,N-di-methyl-1,3-di-aminopropane, 1,3-diaminopropane, 1,6-diamino hexane, 1,6-diamino hexane, 1,8-aminooctane, 1,9-di-aminononane, 1,12-aminododecane, 2-aminobenzylamine, 2-aminobenzimidazole, 2-aminoimidazole, 2,4-di-amino-6-hydroxypyrimidine or benzylamine.

Embodiment 26

The process according to any one of the preceding embodiments, wherein the adsorbent resin comprises polymeric base matrix upon which the ligands (L1 or L2) are supported.

Embodiment 27

The process according to any one of the preceding embodiments, wherein the polymeric base matrix is a natural or synthetic organic polymer, selected from i) natural and synthetic polysaccharides and other carbohydrate based polymers, including agar, alginate, carrageenan, guar gum, gum arabic, gum ghatti, gum tragacanth, karaya gum, locust bean gum, xanthan gum, agaroses, celluloses, pectins, mucins, dextrans, starches, heparins, chitosans, hydroxy starches, hydroxypropyl starches, carboxymethyl starches, hydroxyethyl celluloses, hydroxypropyl celluloses, and carboxymethyl celluloses; ii) synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such polymer functionally, and substituted derivatives thereof; and iii) mixtures thereof.

Embodiment 28

The process according to any one of the preceding embodiments, wherein the adsorbent resin is in the form of a particle.

Embodiment 29

The process according to any one of the preceding embodiments, wherein the aqueous extract of soy protein is obtained by extracting soybeans or a soybean product with water at pH 6.5-7.5.

Embodiment 30

The process according to any one of the preceding embodiments, wherein the aqueous extract of soy protein is obtained by extracting soybeans or a soybean product with water at circa pH 9.0.

Embodiment 31

The process according to any one of the preceding embodiments, wherein the aqueous extract of soy protein is pH-adjusted prior to step (ii), preferably to a pH in the range 2.0-9.0.

Embodiment 32

The process according to embodiment 31, wherein the pH-adjusted soy protein extract is centrifuged or filtered to remove non-soluble material prior to step (ii).

Embodiment 33

A second soy protein composition, depleted in said first type of soy protein, obtained by the process of embodiment 1.

Embodiment 34

A denatured second soy protein composition, obtained by the process of embodiment 5.

Embodiment 35

A first combined soy protein product, obtained by the process of embodiment 15.

Embodiment 36

A second combined soy protein product, obtained by the process of embodiment 16.

Embodiment 37

A third combined soy protein product, obtained by the process of embodiment 17.

EXAMPLES

Example 1

1A) Activation of Agarose Beads

Samples of various high density agarose beads (produced by Upfront Chromatography A/S with an agarose concentration in the range of 3-8% and containing 10% tungsten carbide as a high density filler) having a bead size of 20-350 μm were cross-linked and activated with epichlorhydrin (Aldrich cat.no.:E105-5). The resulting concentrations of epoxy groups were determined to vary in the range of 20-100 mmol/L of beads.

1B) Coupling of Ligands to Activated Beads

The following general procedure was used for coupling ligands to the activated beads described in example 1A.

1) 50 ml of the epoxy-activated beads was washed on a suction filter with 200 ml of deionized water and drained. The drained adsorbent was transferred to a 250 ml plastic bottle
2) The ligand (2.5 g) was dissolved or suspended in 50 ml of deionized water and pH was adjusted to 10.5-12.5 with 2 M NaOH to achieve a fully solubilized ligand solution.
3) The ligand solution was incubated with the drained adsorbent on a roller mixer for 18 hours at room temperature.
4) The adsorbent was washed with five liters of deionized water For ligands which were poorly soluble in water the ligand was dissolved or suspended in 50% ethanol and pH adjusted to 10.5-12.5 with 2 M NaOH. After incubation of the ligand solution with the suction drained adsorbent, the adsorbent was washed with one liter of 50% ethanol followed by four liters of deionized water.

The ligand concentration was determined by acid-base titration of the characteristic functional groups on the coupled ligand.

The following chemical compounds were coupled to epichlorhydrin-activated agarose beads as described in the general procedure above:

4-aminobenzoic acid, 4-mercaptobenzoic acid, 4-aminosalicylic acid, butylamine, hexylamine, octylamine, benzylamine, di-aminopropane, 1.6-diamino hexane (4 and 6% agarose), di-aminooctane, 1,9-di-aminononane, di-aminododecane, 2-aminobenzylamine, neopentylamine, di-butylamine, pentylamine, N,N-di-methyl-di-aminopropane, 2-aminobenzimidazole, 2,4-di-amino-6-hydroxypyrimidine, 2-aminobenzimidazole, 2-aminoimidazole.

1C) Coupling of the Ligand Chloromethylbenzoic Acid to Activated Beads Described in Example 1A 1) 200 ml of the epoxy-activated beads was washed on a suction filter with 800 ml of deionized water and drained. The drained adsorbent was transferred to a 500 ml plastic beaker.
2) 224 ml of deionized water was added. The solution was mixed with a mechanical mixer.
3) 32.5% sodium hydroxide was added to reach a pH of 13.5 (initially 25 ml)
4) 6.7 g of chloromethylbenzoic acid was added.
5) pH was checked every 15 min and 32.5% NaOH was added to keep the pH at 13.5.
6) Every hour 6.7 g of chloromethylbenzoic acid was added.
7) After 8 hours of mixing the adsorbent was washed with five liters of deionized water The ligand concentration was determined by acid-base titration of the characteristic functional groups on the coupled ligand.

1D) Coupling of the Ligand 2-Diethylamino-Ethylchlorid (DEAE) to Activated Beads Described in Example 1A 1) 200 ml of the epoxy-activated beads was washed on a suction filter with 800 ml of deionized water and drained. It was then washed with 600 ml of a 85% N-methylpyrrolidone solution. The drained adsorbent was transferred to a 1000 ml plastic beaker.

2) 200 ml of 85% N-methylpyrrolidone solution was added. The solution was mixed with a mechanical mixer.

3) 12 g of DEAE was added to the solution 4) 50.8 g NaOH was added to the solution 5) After 2 hours the adsorbent was washed with five liters of deionized water The ligand concentration was determined by acid-base titration of the characteristic functional groups on the coupled ligand.

Example 2

The example describes the production of the soy bean extract that was used for the following examples.

Dried soy beans (Cat. No.: 3002 from Unifood Import A/S, Denmark) were milled to create soy bean flour.

Two extraction methods were used:
1. Extraction at near neutral pH
2. Extraction at pH 9.0

Extraction at Near Neutral pH 250 g of soy bean flour was mixed with 1250 ml of deionized water. The suspension was mixed for one hour after which the non-soluble fraction was removed by sieving the extract on a 100 μm nylon filter net. The resulting extract was an unclear, milky liquid with a pH of 6.3 and a conductivity of 5.6 mS/cm.

Extraction at pH 9.0

250 g of soy bean flour was mixed with 1250 ml of deionized water. The suspension was mixed for 1 hour, while during mixing the pH was continuously adjusted to pH 9.0 by the addition of 1 M NaOH. The pH was hereby kept at pH 9.0 during the entire extraction period. Following extraction the non-soluble fraction was removed by sieving the extract on a 100 μm nylon filter net. The resulting extract was an unclear, milky liquid with a pH of 9.0 and a conductivity of 7.0 mS/cm For the experiments performed as packed bed chromatography the extracts were centrifuged at 10,000 rpm to remove precipitated and non-soluble material. After the centrifugation, an upper phase of oil appears. This oil phase was removed before the chromatographic step.

Example 3

SDS PAGE and Dry Matter analytical procedures.

The performance of each of the tested adsorbents described in the following examples was determined by SDS-PAGE gel electrophoresis according to the following general procedure.

25 μL of soy protein sample (centrifuged at 10.000 RPM to remove particles of insoluble material) was mixed with 25 μL tris-glycine sample buffer (LC2676, Novex by Life Technologies, USA). The resulting solution was boiled in water for 5 min under non-reducing conditions. 20 μL of the boiled sample was loaded on to a precast SDS-PAGE gel cassette (4-20% tris-glycine gradient gel (1 mm), EC6025, Novex by Life Technologies, USA). The gel was running for 1 hour at 200 V, 400 mA. The gel was stained with Coomassie blue dye reagent over night (SimplyBlue™ SafeStain, LC6060).

FIG. 1 shows a SDS-PAGE gel of the soy bean extract at pH 9.0, pH 6.0 and pH 4.5. On the gel samples of pure soy bean proteins were also applied to identify some of the different proteins (bands) in the soy extract.

The proteins used to identify the proteins were:
Soy bean trypsin inhibitor (Cat no: T9003, Sigma, USA)
Soy bean lectin (Cat no: L1395, Sigma, USA)
Soy bean Glycinin (G3171, Sigma, USA)
Soy bean β-Conglycinin (C5868, Sigma, USA)
Soy bean lipoxidase (L7395, Sigma, USA)

In the following examples where it is concluded if e.g. the soy bean trypsin inhibitor, the soy bean lectin or other specific proteins are binding/not binding to a specific adsorbent, it is based on this SDS-PAGE gel showing where these specific proteins appear on the gel.

FIG. 1 to Example 3
Lane 1=Soy bean extract pH 9.0
Lane 2=Soy bean extract pH 6.0
Lane 3=Soy bean extract pH 4.5
Lane 4=Soy bean trypsin inhibitor, 1 mg/ml
Lane 5=Soy bean lectin, 1 mg/ml
Lane 6=Soy bean Glycinin, 1 mg/ml
Lane 7=Soy bean β-Conglycinin, 1 mg/ml
Lane 8=Soy bean lipoxidase, 1 mg/ml Dry Matter Determination The amount of non-dialyzable dry matter recovered in the protein eluate of selected examples was determined according to the following general procedure:

A fixed amount of eluate (7.5 ml) was dialyzed for 18 hours against water to eliminate small molecules such as salts and buffer substances from the protein sample (dialysis membrane: Spectra/Por molecularporous membrane tubing a cut off of 6-8 kD, Spectrum Laboratories, USA). Following dialysis the dialyzed protein solution was transferred to a foil beaker and dried over night (24 hours) at 100° C. The amount of dry matter (protein) was calculated as the weight of the beaker after drying minus the weight of the beaker. Quantitative amino acid analysis generally confirmed that more than 90% of the dry matter was indeed protein related.

Example 4

Adsorbents produced according to EXAMPLE 1 were tested for the ability to bind soy bean proteins at pH 4.5. The following ligands were tested:

4-mercaptobenzoic acid (coupled to 4 and 6% agarose beads), chloromethylbenzoic acid (coupled to 6% agarose beads) and 4-aminosalicylic acid (coupled 6% agarose beads).

Procedure 1 ml of adsorbent was transferred and packed into a small open-top plastic column (Poly-Prep Chromatography Column cat. No.: 731-1550 Biorad, USA) to form a packed bed of approx. 20 mm bed height. The flow rate applied through the packed was approx. 0.5 ml/min for all tests. After packing the adsorbent was equilibrated with 10 ml 10 mM sodium citrate pH 4.5. The soy extract (produced at near neutral pH according to EXAMPLE 2) was pH-adjusted with 1 M HCl to pH 4.5 and centrifuged at 10,000 RPM to remove precipitated and non-soluble material. 1.5 ml of the centrifuged extract was loaded onto the column. The flow through (non-bound proteins) was collected in one fraction. The column was then washed with 5 ml of deionized water. The flow through (non-bound and loosely bound proteins) was collected in one 5 ml fraction. The bound proteins were subsequently released from the column (eluted) by applying 10 ml 50 mM NaOH. The flow through (eluted proteins, eluate) was collected in one 10 ml fraction and pH in the eluate fraction was immediately adjusted to pH 7.0 by addition of 1 M HCl. The performance of the adsorbent was determined by SDS-PAGE (as described in EXAMPLE 3). See FIG. 2. Arrows indicate bands identified in EXAMPLE 3 using purified soy proteins The results indicated that the tested aromatic acid ligands bound essentially all the applied amount of protein including trypsin inhibitor and soy bean lectin. For the 4-mercaptobenzoic acid ligand (coupled to 4 and 6% agarose beads) see lane 2 and 4 representing the run-through fraction containing non-bound proteins which is practically devoided of significant protein bands, while the trypsin inhibitor, soy bean lectin and other proteins are found in the eluate (see lane 3 and 5). For the chloromethylbenzoic acid ligand (coupled to 6% agarose beads) see lane 6 representing the run-through fraction containing non-bound proteins which is practically devoided of significant protein bands, while the trypsin inhibitor, soy bean lectin and other proteins are found in the eluate (see lane 6). The 4-aminosalicylic acid ligand (coupled 6% agarose beads) see lane 7 representing the run-through fraction containing non-bound proteins which is practically devoided of significant protein bands, while the trypsin inhibitor, soy bean lectin and other proteins are found in the eluate (see lane 8).

Figure 2:
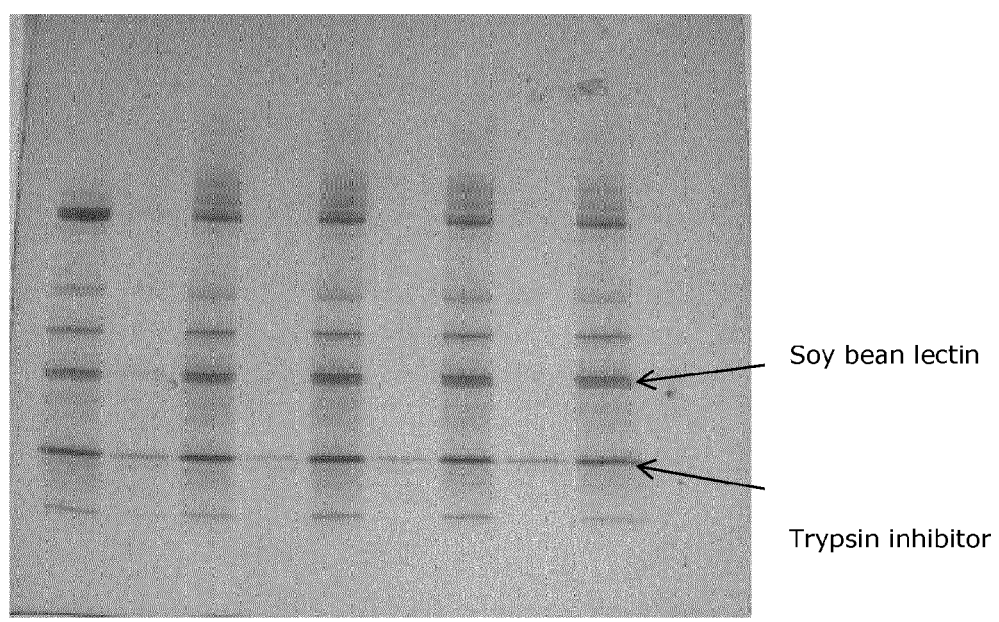
Figure 3A:
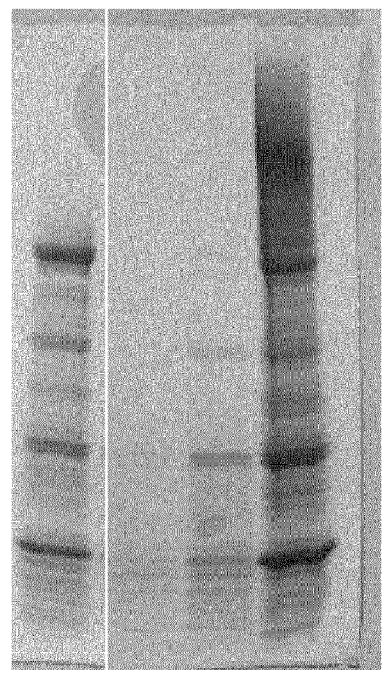
Figure 3B:
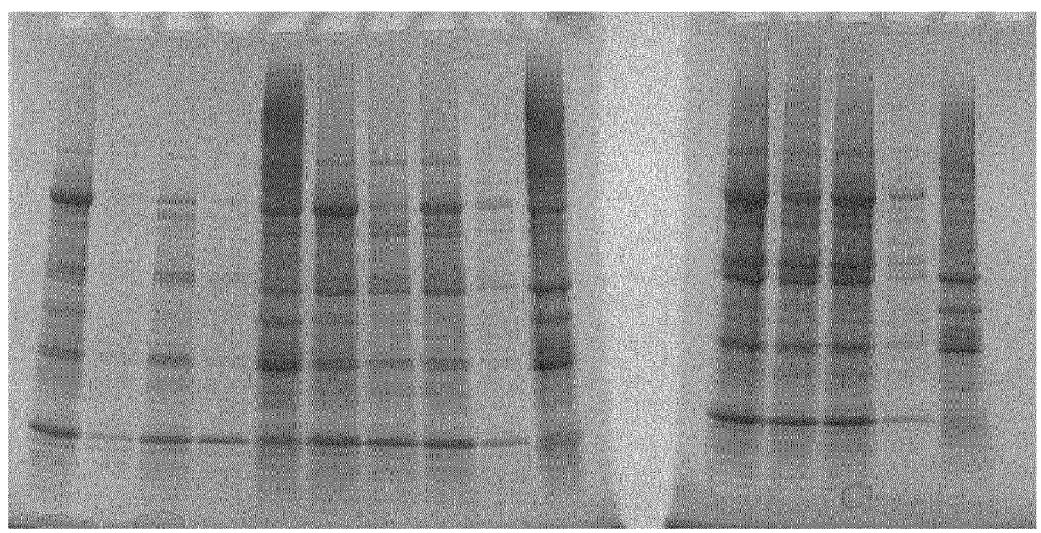

FIG. 2 for Example 4

Lane 1=soy extract at pH 4.5

Lane 2=Flow through (non-bound proteins) from load of adsorbent with the ligand 4-mercaptobenzoic acid (4% agarose beads)

Lane 3=Eluate (Bound and subsequently released proteins) from adsorbent with the ligand 4-mercaptobenzoic acid (4% agarose beads)

Lane 4=Flow through (non-bound proteins) from load of adsorbent with the ligand 4-mercaptobenzoic acid (6% agarose beads)

Lane 5=Eluate (Bound and subsequently released proteins) from adsorbent with the ligand 4-mercaptobenzoic acid (6% agarose beads)

Lane 6=Flow through (non-bound proteins) from load of adsorbent with the ligand 4-aminosalicylic acid (6% agarose beads)

Lane 7=Eluate (Bound and subsequently released proteins) from adsorbent with the ligand 4-aminosalicylic acid (6% agarose beads)

Lane 8=Flow through (non-bound proteins) from load of adsorbent with the ligand chloromethylbenzoic acid (6% agarose)

Lane 9=Eluate (Bound and subsequently released proteins) from adsorbent with the ligand chloromethylbenzoic acid (6% agarose)

Example 5

An adsorbent with the ligand 4-aminobenzoic acid produced according to EXAMPLE 1 (4% agarose), (the ligand concentration was determined with titration to be 30 mmol/L adsorbent) was tested for the ability to bind soy bean proteins at respectively pH 4.5, 5.0, 5.5 and 6.0.

Procedure

Column preparation and flow rate as per Example 4. After packing the adsorbent was equilibrated with 10 ml 10 mM sodium citrate respectively pH 4.5, 5.0, 5.5 and 6.0. The soy extract (produced at near neutral pH according to EXAMPLE 2) was pH-adjusted with 1 M HCl to respectively pH 6.0, 5.5, 5.0 and 4.5. The extract was centrifuged at 10,000 RPM to remove non-soluble and precipitated material. 10 ml of the centrifuged extract was loaded onto the column. The flow through (non-bound proteins) was collected in one 10 ml fraction for experiment performed at pH 4.5, two fractions of 5 ml for experiments performed at pH 5.0, 5.5 and 6.0. The adsorbent was washed with 5 ml of deionized water. The flow through (non-bound and loosely bound proteins) was collected in one 5 ml fraction. The bound proteins were subsequently released from the column (eluted) by applying 10 ml 50 mM NaOH. The flow through (eluted proteins, eluate) was collected in one 10 ml fraction and pH in the eluate fraction was immediately adjusted to pH 7.0 by addition of 1 M The performance of the adsorbent was determined by SDS-PAGE (as described in EXAMPLE 3). See FIGS. 3a and 3b.

The results indicated that the tested 4-aminobenzoic acid ligand binds practically all the applied amount of protein including trypsin inhibitor and soy bean lectin at pH 4.5 (see lane 2 representing the run-through fraction containing non-bound proteins is practically devoid of significant protein bands) while the trypsin inhibitor, soy bean lectin and other proteins are eluted with the 50 mM NaOH solution (see lane 4).

At pH 5.0 only a minor fraction of the trypsin inhibitor binds to the 4-aminobenzoic acid ligand (see lane 7 representing the second flow through fraction where the intensity of the trypsin inhibitor band is similar to the soy bean extract in lane 6 meaning that the protein does not bind to the adsorbent also see lane 8 representing the wash that also contains the trypsin inhibitor). Other soy proteins bind to the adsorbent and are eluted with the 50 mM NaOH solution (see lane 9, the eluate contains a low amount of trypsin inhibitor, the band representing this protein is very weak).

At pH 5.5 the trypsin inhibitor does not bind to the 4-aminobenzoic acid ligand (see lane 11 and 12 representing the run-through fractions containing non-bound proteins where the intensity of trypsin inhibitor band is the same as in lane 10 which represent the soy extract loaded onto the column). Other soy proteins bind to the adsorbent and are eluted with the 50 mM NaOH solution (see lane 14, the eluate does not contain trypsin inhibitor).

At pH 6.0 most of the applied protein is recovered in the two flow through fractions when the soy extract is loaded onto the adsorbent. The 4-aminobenzoic acid ligand only binds a small amount of protein and no trypsin inhibitor at all (see lane 16 and 17 representing the run-through fractions containing non-bound proteins where the intensity of all major bands are almost the same as in lane 15 which represent the soy extract loaded onto the column). The bound proteins are eluted with the 50 mM NaOH solution (see lane 19, the eluate does not contain trypsin inhibitor).

FIG. 3a, Example 5

Lane 1=soy extract at pH 4.5

Lane 2=Flow through (non-bound proteins) from load of adsorbent with the ligand 4-aminobenzoic acid (4% agarose beads) at pH 4.5.

Lane 3=Wash (non-bound and loosely bound proteins) of the adsorbent with the ligand 4-aminobenzoic acid (4% agarose beads)

Lane 4=Eluate (Bound and subsequently released proteins) from adsorbent with the ligand 4-aminobenzoic acid (4% agarose beads)

Lane 5=soy extract at pH 5.0

Lane 6=Flow through fraction 1 (non-bound proteins) from load of adsorbent with the ligand 4-aminobenzoic acid (4% agarose beads) at pH 5.0.

Lane 7=Flow through fraction 2 (non-bound proteins) from load of adsorbent with the ligand 4-aminobenzoic acid (4% agarose beads) at pH 5.0.

Lane 8=Wash (non-bound and loosely bound proteins) of the adsorbent with the ligand 4-aminobenzoic acid (4% agarose beads)

Lane 9=Eluate (Bound and subsequently released proteins) from adsorbent with the ligand 4-aminobenzoic acid (4% agarose beads) at pH 5.0

Lane 10=soy extract at pH 5.5

Lane 11=Flow through fraction 1 (non-bound proteins) from load of adsorbent with the ligand 4-aminobenzoic acid (4% agarose beads) at pH 5.5.

Lane 12=Flow through fraction 2 (non-bound proteins) from load of adsorbent with the ligand 4-aminobenzoic acid (4% agarose beads) at pH 5.5.

Lane 13=Wash (non-bound and loosely bound proteins) of the adsorbent with the ligand 4-aminobenzoic acid (4% agarose beads)

Lane 14=Eluate (Bound and subsequently released proteins) from adsorbent with the ligand 4-aminobenzoic acid (4% agarose beads) at pH 5.5

Lane 15=soy extract at pH 6.0

Lane 16=Flow through fraction 1 (non-bound proteins) from load of adsorbent with the ligand 4-aminobenzoic acid (4% agarose beads) at pH 6.0.

Lane 17=Flow through fraction 2 (non-bound proteins) from load of adsorbent with the ligand 4-aminobenzoic acid (4% agarose beads) at pH 6.0.

Lane 18=Wash (non-bound and loosely bound proteins) of the adsorbent with the ligand 4-aminobenzoic acid (4% agarose beads)

Lane 19=Eluate (Bound and subsequently released proteins) from adsorbent with the ligand 4-aminobenzoic acid (4% agarose beads) at pH 6.0

Example 6

The example shows how the trypsin inhibitor was eluted selectively from an adsorbent coupled with the ligand 4-mercaptobenzoic acid (produced as described in EXAMPLE 1), (the ligand concentration was determined with titration to be 51 mmol/L adsorbent) where the all the available proteins in the extract have been bound at pH 4.5. During elution the pH was stepwise increased by applying respectively a) 10 mM sodium citrate pH 6.0, b) 10 mM di-potassium hydrogen phosphate pH 8.0 and c) 50 mM NaOH.

Procedure

Column preparation and flow rate as per Example 4. After packing the adsorbent was equilibrated with 10 ml 10 mM sodium citrate pH 4.5. The soy extract (produced at near neutral pH according to EXAMPLE 2) was pH-adjusted with 1 M HCl to 4.5. The extract was centrifuged at 10,000 RPM to remove non-soluble and precipitated material. 10 ml of the centrifuged extract was loaded onto the column. The flow through (non-bound proteins) was collected in one fraction of 10 ml. The adsorbent was washed with 5 ml of deionized water. The flow through (non-bound and loosely bound proteins) was collected in one 5 ml fraction. The bound proteins were subsequently released from the column (eluted) by applying the following buffers:

10 mM sodium citrate pH 6.0, 10 ml, the flow through (eluted proteins, eluate) was collected in one 10 ml fraction.

10 mM di-potassium hydrogenphosphate pH 8.0, 10 ml, the flow through (eluted proteins, eluate) was collected in one 10 ml fraction.

50 mM NaOH, 10 ml, the flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIG. 4. Arrows indicate bands identified in EXAMPLE 3 using purified soy proteins.

The results indicate that the adsorbent bound essentially all the proteins applied to the column (see lane 2 representing the run-through fraction containing non-bound proteins is practically devoid of significant protein bands) while the trypsin inhibitor was eluted selectively (at pH 6.0, see lane 3) from the 4-mercaptobenzoic acid ligand before the other proteins (including the Soy bean lectin) which were eluted by the pH 8 buffer and 50 mM NaOH solution respectively (see lane 4 and 5).

Figure 4:
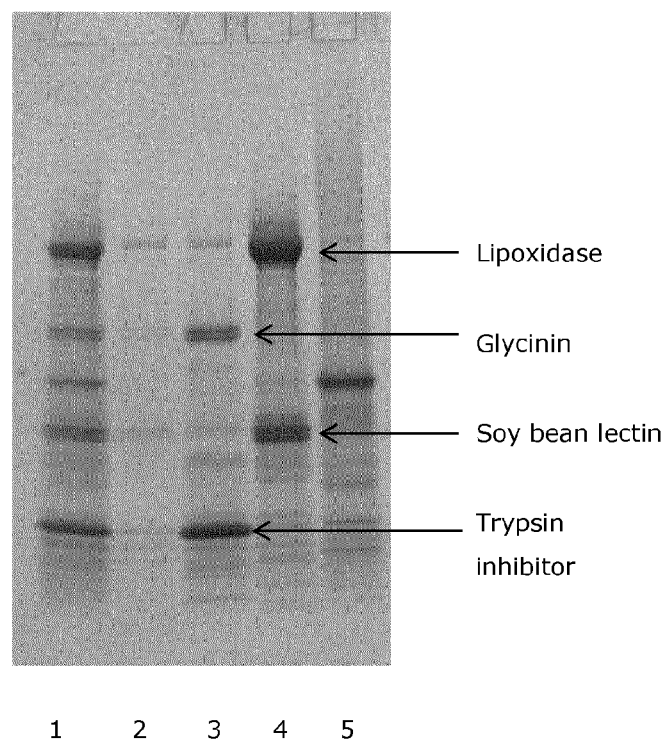
Figure 5:
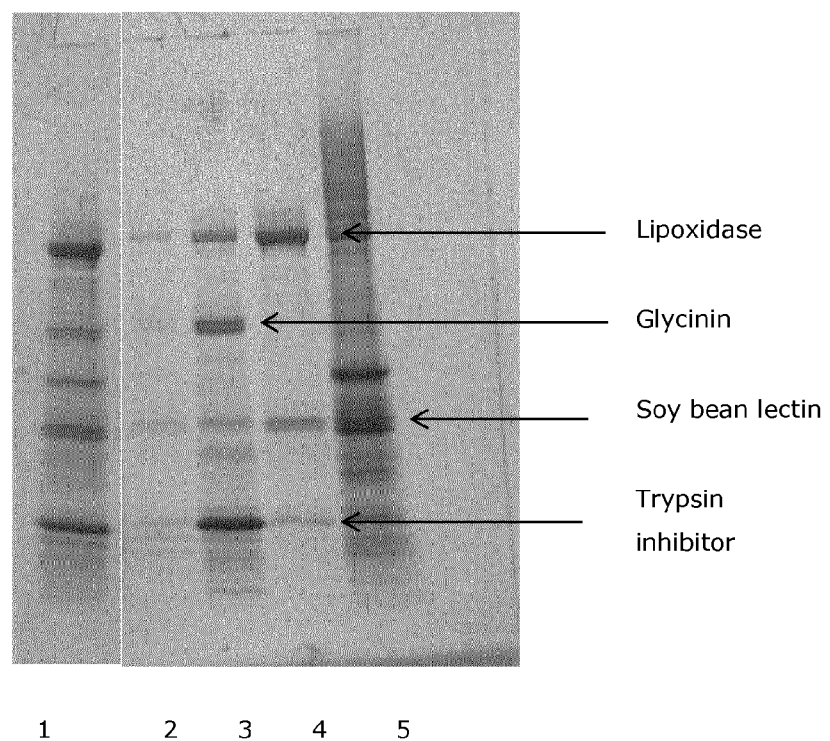

FIG. 4 for Example 6

Lane 1=soy extract at pH 4.5

Lane 2=Flow through (non-bound proteins) from load of adsorbent with the ligand 4-mercaptobenzoic acid at pH 4.5.

Lane 3=Eluate (Bound and subsequently released proteins) from adsorbent with the ligand 4-mercaptobenzoic acid at pH 6.0

Lane 4=Eluate (Bound and subsequently released proteins) from adsorbent with the ligand 4-mercaptobenzoic acid at pH 8.0

Lane 5=Eluate (Bound and subsequently released proteins) from adsorbent with the ligand 4-mercaptobenzoic acid with 50 mM NaOH Example 7

The example shows how the trypsin inhibitor was eluted selectively from an adsorbent coupled with the ligand 4-mercaptobenzoic acid (produced as described in EXAMPLE 1), (the ligand concentration was determined with titration to be 51 mmol/L adsorbent) where the all available proteins have been bound at pH 4.5. During elution the salt concentration was step wise increased at a fixed pH-value by applying respectively a) 10 mM sodium citrate+50 mM NaCl pH 6.0, b) 10 mM sodium citrate, 200 mM NaCl pH 6.0 and finally high pH using c) 50 mM NaOH.

Procedure

Column preparation and flow rate as per Example 4. After packing the adsorbent was equilibrated with 10 ml 10 mM sodium citrate pH 4.5. The soy extract (produced at near neutral pH according to EXAMPLE 2) was pH-adjusted with 1 M HCl to 4.5. The extract was centrifuged at 10,000 RPM to remove non-soluble and precipitated material. 10 ml of the centrifuged extract was loaded onto the column. The flow through (non-bound proteins) was collected in one fraction of 10 ml. The adsorbent was washed with 5 ml of deionized water. The flow through (non-bound and loosely bound proteins) was collected in one 5 ml fraction. The bound proteins were subsequently released from the column (eluted) by applying the following buffers:

a) 10 mM sodium citrate, 50 mM NaCl pH 6.0, 10 ml, the flow through (eluted proteins, eluate) was collected in one 10 ml fraction.

b) 10 mM sodium citrate, 200 mM NaCl pH 6.0, 10 ml, the flow through (eluted proteins, eluate) was collected in one 10 ml fraction.

c) 50 mM NaOH, 10 ml, the flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIG. 5. Arrows indicate bands identified in EXAMPLE 3 using purified soy proteins.

The results indicate that the adsorbent bound essentially all the proteins applied to the column (see lane 2 representing the run-through fraction containing non-bound proteins is practically devoid of significant protein bands) while the trypsin inhibitor was eluted selectively (at pH 6 with 50 mM NaCl, see lane 3) from the 4-mercaptobenzoic acid ligand and the soy bean lipoxidase is selectively eluted (at pH 6.0 with 200 mM NaCl see lane 4) before the other proteins (including the Soy bean lectin) with 50 mM NaOH (see lane 5)

Lane 1=soy extract at pH 4.5
Lane 2=Flow through (non-bound proteins) from load of adsorbent with the ligand 4-mercaptobenzoic acid at pH 4.5.
Lane 3=Eluate (Bound and subsequently released proteins) from adsorbent with the ligand 4-mercaptobenzoic acid at pH 6.0, 50 mM NaCl
Lane 4=Eluate (Bound and subsequently released proteins) from adsorbent with the ligand 4-mercaptobenzoic acid at pH 6.0, 200 mM NaCl
Lane 5=Eluate (Bound and subsequently released proteins) from adsorbent with the ligand 4-mercaptobenzoic acid with 50 mM NaOH Example 8

The example shows how the trypsin inhibitor and soy bean lectin were eluted selectively from an adsorbent coupled with the ligand 4-aminobenzoic acid (produced as described in EXAMPLE 1), (the ligand concentration was determined with titration to be 30 mmol/L adsorbent) where the all the available proteins in the extract were initially bound at pH 4.5. During elution the pH was step wise increased by applying dilute buffers with increasing pH values.

Procedure

Column preparation and flow rate as per Example 4. After packing the adsorbent was equilibrated with 10 ml 10 mM sodium citrate pH 4.5. The soy extract (produced at near neutral pH according to EXAMPLE 2) was pH-adjusted with 1 M HCl to 4.5. The extract was centrifuged at 10,000 RPM to remove non-soluble and precipitated material. 10 ml of the centrifuged extract was loaded onto the column. The flow through (non-bound proteins) was collected in one fraction of 10 ml. The adsorbent was washed with 5 ml of deionized water. The flow through (non-bound and loosely bound proteins) was collected in one 5 ml fraction.

The bound proteins were subsequently released from the column (eluted) by applying the following buffers:

10 mM sodium citrate pH 5.75, 10 ml, the flow through (eluted proteins, eluate) was collected in one 10 ml fraction.
10 mM di-potassiumhydrogenphosphate pH 6.0, 10 ml, the flow through (eluted proteins, eluate) was collected in one 10 ml fraction.
10 mM di-potassiumhydrogenphosphate pH 6.5, 10 ml, the flow through (eluted proteins, eluate) was collected in one 10 ml fraction.
10 mM di-potassiumhydrogenphosphate pH 7.0, 10 ml, the flow through (eluted proteins, eluate) was collected in one 10 ml fraction.
10 mM di-potassiumhydrogenphosphate pH 7.5, 10 ml, the flow through (eluted proteins, eluate) was collected in one 10 ml fraction.
10 mM di-potassiumhydrogenphosphate pH 8.0, 10 ml, the flow through (eluted proteins, eluate) was collected in one 10 ml fraction.
50 mM NaOH, 10 ml, the flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIG. 6. Arrows indicate bands identified in EXAMPLE 3 using purified soy proteins.

The results indicate that the adsorbent bound essentially all the proteins applied to the column (see lane 2 representing the run-through fraction containing non-bound proteins is practically devoid of significant protein bands) while the trypsin inhibitor was eluted selectively (at pH 5.75, see lane 4) from the 4-aminobenzoic acid ligand. The soy bean lectin is selectively eluted (at pH 6.5 see lane 6). The soy bean lipoxidase is selectively eluted (at pH 7.0 see lane 7) before the other proteins which were eluted by the pH 7.5, pH 8 buffer and 50 mM NaOH solution respectively (see lane 8, 9 and 10).

Figure 6:
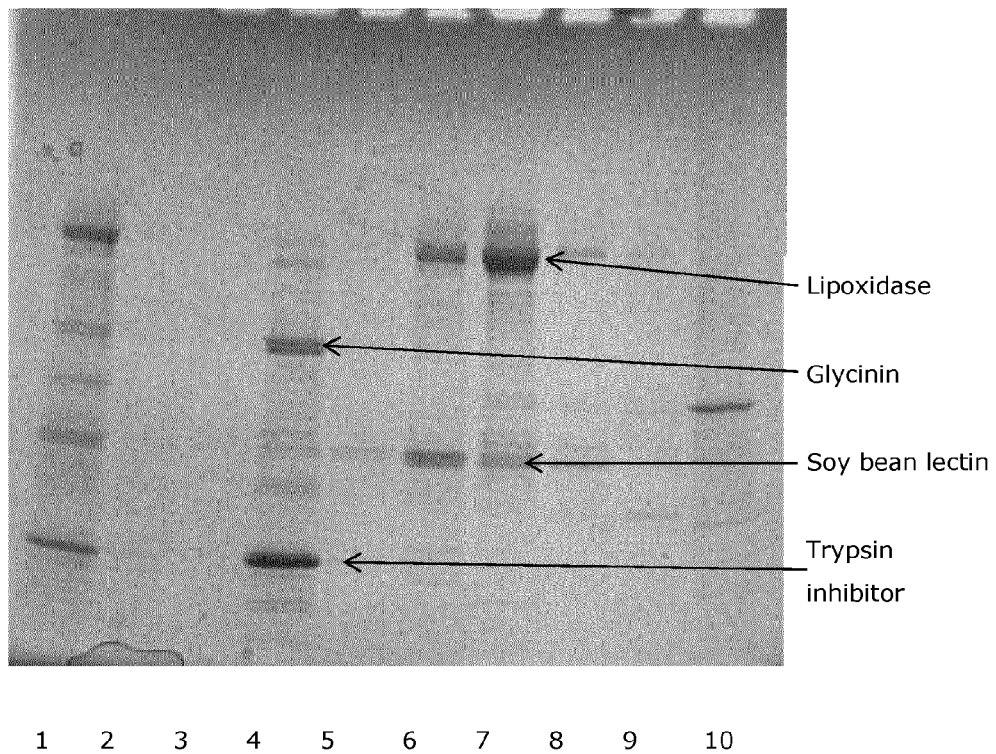

FIG. 6 for Example 8

Lane 1=soy extract at pH 4.5
Lane 2=Flow through (non-bound proteins) from load of adsorbent with the ligand 4-aminobenzoic acid (4% agarose beads) at pH 4.5.
Lane 3=Wash (non-bound and loosely bound proteins) of the adsorbent with the ligand 4-aminobenzoic acid (4% agarose beads)
Lane 4=Eluate (Bound and subsequently released proteins) from adsorbent with the ligand 4-aminobenzoic acid (4% agarose beads) at pH 5.75
Lane 5=Eluate (Bound and subsequently released proteins) from adsorbent with the ligand 4-aminobenzoic acid (4% agarose beads) at pH 6.0
Lane 6=Eluate (Bound and subsequently released proteins) from adsorbent with the ligand 4-aminobenzoic acid (4% agarose beads) at pH 6.5
Lane 7=Eluate (Bound and subsequently released proteins) from adsorbent with the ligand 4-aminobenzoic acid (4% agarose beads) at pH 7.0
Lane 8=Eluate (Bound and subsequently released proteins) from adsorbent with the ligand 4-aminobenzoic acid (4% agarose beads) at pH 7.5
Lane 9=Eluate (Bound and subsequently released proteins) from adsorbent with the ligand 4-aminobenzoic acid (4% agarose beads) at pH 8.0
Lane 10=Eluate (Bound and subsequently released proteins) from adsorbent with the ligand 4-aminobenzoic acid (4% agarose beads) with 50 mM NaOH Example 9

The example shows how the trypsin inhibitor was eluted selectively from an adsorbent coupled with the ligand 4-aminobenzoic acid (produced according to EXAMPLE 1), (the ligand concentration was determined with titration to be 30 mmol/L adsorbent) where the all the available proteins have been bound at pH 4.5. During elution the pH was stepwise increased to respectively a) 10 mM sodium citrate pH 5.0, b) 10 mM sodium citrate pH 5.25, c) 10 mM sodium citrate pH 5.5, d) 10 mM sodium citrate pH 5.75 and e) 50 mM NaOH.

Procedure

Column preparation and flow rate as per Example 4. After packing the adsorbent was equilibrated with 10 ml 10 mM sodium citrate pH 4.5. The soy extract (produced at near neutral pH according to EXAMPLE 2) was pH-adjusted with 1 M HCl to 4.5. The extract was centrifuged at 10,000 RPM to remove non-soluble and precipitated material. 10 ml of the centrifuged extract was loaded onto the column. The flow through (non-bound proteins) was collected in one fraction of 10 ml. The adsorbent was washed with 5 ml of deionized water. The flow through (non-bound and loosely bound proteins) was collected in one 5 ml fraction.

The bound proteins were subsequently released from the column (eluted) by applying the following buffers:
  a) 10 mM sodium citrate pH 5.0, 10 ml, the flow through (eluted proteins, eluate) was collected in one 10 ml fraction.
  b) 10 mM sodium citrate pH 5.25, 10 ml, the flow through (eluted proteins, eluate) was collected in one 10 ml fraction.
  c) 10 mM sodium citrate pH 5.5, 10 ml, the flow through (eluted proteins, eluate) was collected in one 10 ml fraction.
  d) 10 mM sodium citrate pH 5.75, 10 ml, the flow through (eluted proteins, eluate) was collected in one 10 ml fraction.
  e) 50 mM NaOH, 10 ml, the flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIG. 7. Arrows indicate bands identified in EXAMPLE 3 using purified soy proteins.

The results indicate that the adsorbent bound essentially all the proteins applied to the column (see lane 2 representing the run-through fraction containing non-bound proteins is practically devoid of significant protein bands) while the trypsin inhibitor was eluted selectively (at pH 5.0 to pH 5.5, see lane 4 to lane 6) from the 4-aminoobenzoic acid ligand before the other proteins (including the Soy bean lectin) which were eluted by the pH 5.75 buffer and 50 mM NaOH solution respectively (see lane 7 and 8).

Figure 7:
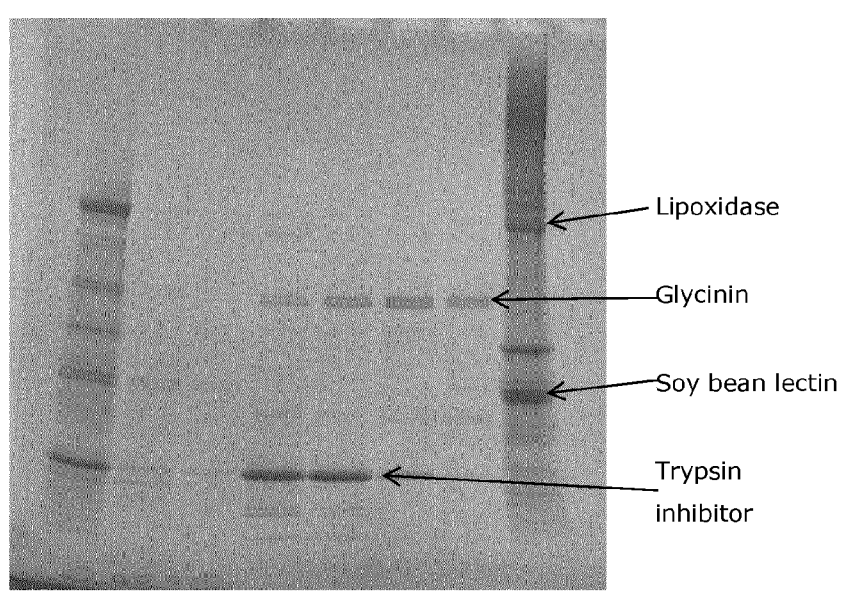

FIG. 7 for Example 9
  Lane 1=soy extract at pH 4.5
  Lane 2=Flow through (non-bound proteins) from load of adsorbent with the ligand 4-aminobenzoic acid (4% agarose beads) at pH 4.5.
  Lane 3=Wash (non-bound and loosely bound proteins) of the adsorbent with the ligand 4-aminobenzoic acid (4% agarose beads)
  Lane 4=Eluate (Bound and subsequently released proteins) from adsorbent with the ligand 4-aminobenzoic acid (4% agarose beads) at pH 5.0
  Lane 5=Eluate (Bound and subsequently released proteins) from adsorbent with the ligand 4-aminobenzoic acid (4% agarose beads) at pH 5.25
  Lane 6=Eluate (Bound and subsequently released proteins) from adsorbent with the ligand 4-aminobenzoic acid (4% agarose beads) at pH 5.5
  Lane 7=Eluate (Bound and subsequently released proteins) from adsorbent with the ligand 4-aminobenzoic acid (4% agarose beads) at pH 5.75
  Lane 8=Eluate (Bound and subsequently released proteins) from adsorbent with the ligand 4-aminobenzoic acid (4% agarose beads) with 50 mM NaOH Example 10

Isolation of soy bean proteins with anion exchanger. Adsorbent coupled with the ligand DEAE produced according to example 1D, (the ligand concentration was determined with titration to be 104 mmol/L adsorbent) was tested for the ability to bind soy bean proteins at pH 6.0.

Procedure

Column preparation and flow rate as per Example 4. After packing the adsorbent was equilibrated with 10 ml 0.1 M sodium citrate pH 6.0 followed by 10 ml 10 mM sodium citrate pH 6.0. The soy extract (produced at near neutral pH according to EXAMPLE 2) was pH-adjusted with 1 M HCl to pH 6.0 and centrifuged at 10,000 RPM to remove precipitated and non-soluble material. 7.5 ml of the centrifuged extract was loaded onto the column. The flow through (non-bound proteins) was collected in one 7.5 ml fraction. The column was then washed with 5 ml of deionized water. The flow through (non-bound and loosely bound proteins) was collected in one fraction.

The bound proteins were subsequently released from the column (eluted) by applying 10 ml 50 mM NaOH. The flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIG. 8. Arrows indicate bands identified in EXAMPLE 3 using purified soy proteins.

The results indicated that the anion exchanger has a low binding capacity; it only binds a small fraction of the soy proteins, and especially the trypsin inhibitor does not bind very well. Lane 2 represents the run-through fraction containing non-bound proteins which contain practically all the trypsin inhibitor and all significant protein bands (including the soy bean lectin). The soy bean proteins are found in the eluate (see lane 4) containing a very small amount of trypsin inhibitor and soy bean lectin.

Figure 8:
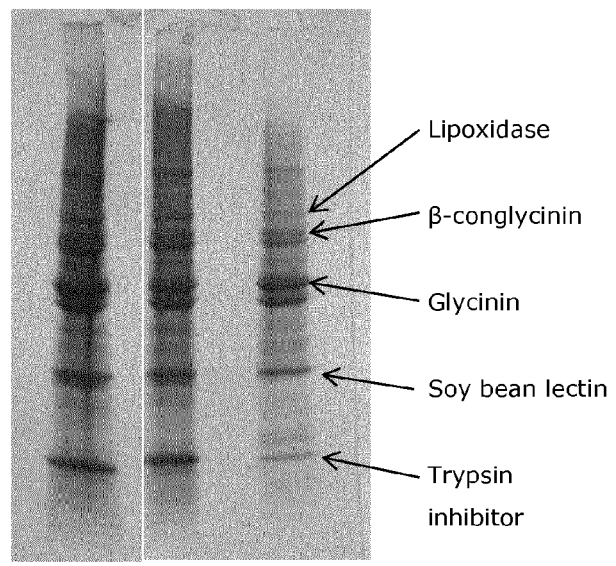

FIG. 8 for Example 10
  Lane 1=soy extract at pH 6.0
  Lane 2=Flow through (non-bound proteins) from load of adsorbent with the ligand DEAE at pH 6.0.
  Lane 3=Wash (non-bound and loosely bound proteins) of the adsorbent with the ligand DEAE
  Lane 4=Eluate (Bound and subsequently released proteins) from adsorbent with the ligand DEAE Example 11

Adsorbents produced according to EXAMPLE 1 were tested for the ability to bind soy bean proteins at pH 6.0. The following ligands were tested:

Butylamine (coupled to 6% agarose), Hexylamine (coupled to 6% agarose), Octylamine (coupled to 6% agarose), Benzylamine (coupled to 4% agarose), Benzylamine (coupled to 6% agarose)

Procedure

Column preparation and flow rate as per Example 4. After packing the adsorbent was equilibrated with 10 ml 10 mM sodium citrate pH 6.0. The soy extract (produced at near neutral pH according to EXAMPLE 2) was pH-adjusted with 1 M HCl to pH 6.0 and centrifuged at 10,000 RPM to remove precipitated and non-soluble material. 1.5 ml of the centrifuged extract was loaded onto the column. The flow through (non-bound proteins) was collected in one 1.5 ml fraction. The column was then washed with 5 ml of deionized water. The flow through (non-bound and loosely bound proteins) was collected in one 5 ml fraction.

The bound proteins were subsequently released from the column (eluted) by applying 10 ml 50 mM NaOH. The flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIGS. 9a and 9b. Arrows indicate bands identified in EXAMPLE 3 using purified soy proteins.

The results indicated that the tested alkylamine ligands bind practically all the applied amount of trypsin inhibitor. The binding of soy bean lectin was very low. Only a fraction of the other soy proteins bind to the ligands.

For the butylamine ligand (coupled to 6% agarose) see lane 2 representing the run-through fraction containing non-bound proteins which contain a small amount of trypsin inhibitor and all significant protein bands (including the soy bean lectin) are presented as well. The trypsin inhibitor and other proteins are found in the eluate (see lane 3)

For the hexylamine ligand (coupled to 6% agarose) see lane 4 representing the run-through fraction containing non-bound proteins which is depleted from trypsin inhibitor. All significant protein bands (including the soy bean lectin) are presented. The trypsin inhibitor and other proteins are found in the eluate (see lane 5).

For the octylamine (coupled to 6% agarose) see lane 6 representing the run-through fraction containing non-bound proteins which contain a very small amount of trypsin inhibitor and all significant protein bands (including the soy bean lectin) are presented as well. The trypsin inhibitor and other proteins are found in the eluate (see lane 7)

Benzylamine (coupled to 4 and 6% agarose) see lane 8 and 10 representing the run-through fractions containing non-bound proteins which are depleted from trypsin inhibitor. All significant protein bands (including the soy bean lectin) are presented as well. The trypsin inhibitor and other proteins are found in the eluate (see lane 9 and 11).

Figure 9A:
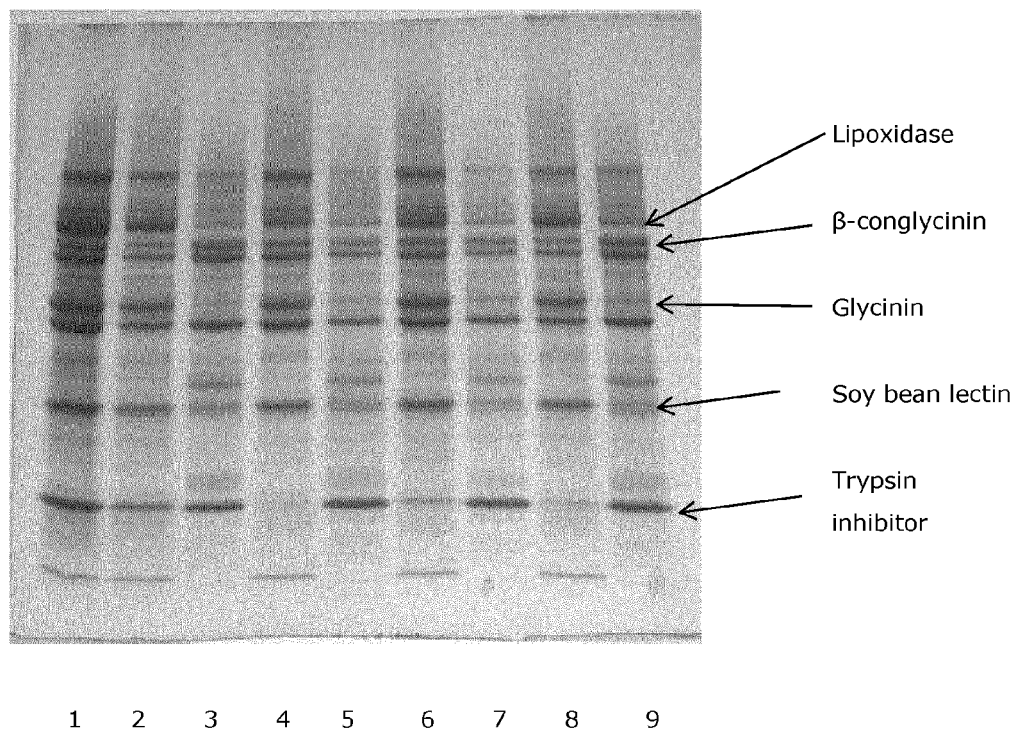

FIG. 9a for Example 11

Lane 1=soy extract at pH 6.0

Lane 2=Flow through (non-bound proteins) from load of adsorbent with the ligand Butylamine (coupled to 6% agarose)

Lane 3=Eluate (Bound and subsequently released proteins) from adsorbent with the ligand Butylamine (coupled to 6% agarose)

Lane 4=Flow through (non-bound proteins) from load of adsorbent with the ligand Hexylamine (coupled to 6% agarose)

Lane 5=Eluate (Bound and subsequently released proteins) from adsorbent with the Hexylamine (coupled to 6% agarose)

Lane 6=Flow through (non-bound proteins) from load of adsorbent with the ligand Octylamine (coupled to 6% agarose)

Lane 7=Eluate (Bound and subsequently released proteins) from adsorbent with the ligand Octylamine (coupled to 6% agarose)

Lane 8=Flow through (non-bound proteins) from load of adsorbent with the ligand Benzylamine (coupled to 4% agarose)

Lane 9=Eluate (Bound and subsequently released proteins) from adsorbent with the ligand Benzylamine (coupled to 4% agarose)

Figure 9B:
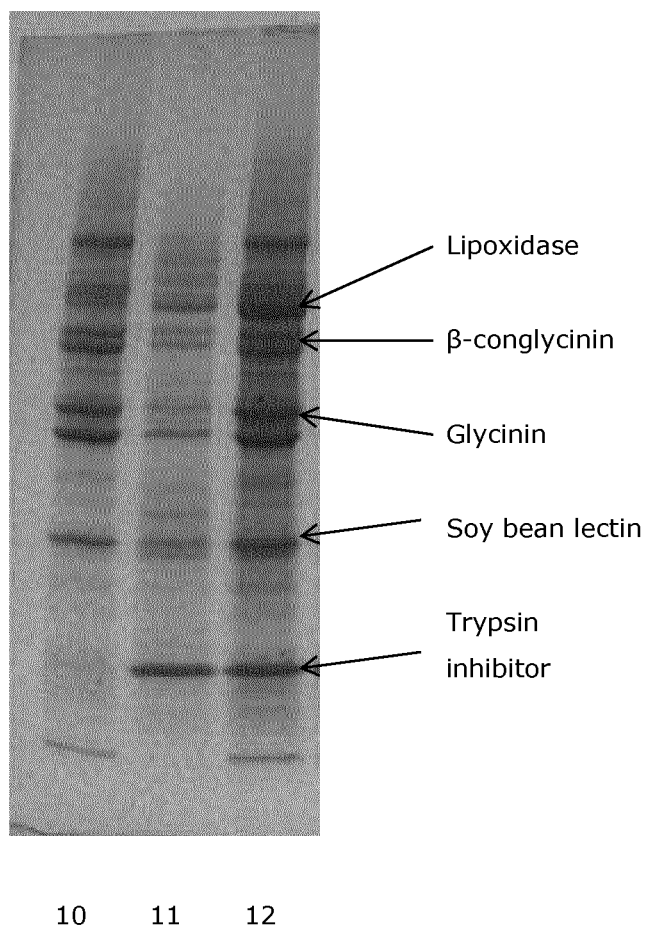

FIG. 9b for Example 11

Lane 10=Flow through (non-bound proteins) from load of adsorbent with the ligand Benzylamine (coupled to 6% agarose)

Lane 11=Eluate (Bound and subsequently released proteins) from adsorbent with the ligand Benzylamine (coupled to 6% agarose)

Lane 12=soy extract at pH 6.0

Example 12

Adsorbents produced according to EXAMPLE 1 were tested for the ability to bind soy bean proteins at pH 6.0. The following ligands (=L2) were tested:

Di-aminopropane, 1.6-diamino hexane (4 and 6% agarose), di-aminooctane, 1,9-di-aminononane, di-aminododecane, 2-aminobenzylamine, Neopentylamine, di-butylamine, Pentylamine, N,N-di-methyl-di-aminopropane, 2-aminobenzimidazole (4 and 6% agarose), 2,4-di-amino-6-hydroxypyrimidine, 2-aminoimidazole Procedure Column preparation and flow rate as per Example 4. After packing the adsorbent was equilibrated with 10 ml 10 mM sodium citrate pH 6.0. The soy extract (produced at near neutral pH according to EXAMPLE 2) was pH-adjusted with 1 M HCl to pH 6.0 and centrifuged at 10,000 RPM to remove precipitated and non-soluble material. 7.5 ml of the centrifuged extract was loaded onto the column. The flow through (non-bound proteins) was collected in one 7.5 ml fraction. The column was then washed with 5 ml of deionized water. The flow through (non-bound and loosely bound proteins) was collected in one 5 ml fraction.

The bound proteins were subsequently released from the column (eluted) by applying 10 ml 50 mM NaOH. The flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIGS. 10a, 10b, 10c and 10d. Arrows indicate bands identified in EXAMPLE 3 using purified soy proteins.

As can be seen from the figures the tested adsorbents separate the soy proteins to various degrees, dependent on the ligand structure.

Lane 1=soy extract at pH 6.0

Lane 2=Flow through (non-bound proteins) from load of adsorbent with the ligand 1.6-diamino hexane (coupled to 6% agarose)

Lane 3=Eluate (Bound and subsequently released proteins) from adsorbent with the ligand 1.6-diamino hexane (coupled to 6% agarose)

Lane 4=Flow through (non-bound proteins) from load of adsorbent with the ligand 1.6-diaminohexane (coupled to 4% agarose)

Lane 5=Eluate (Bound and subsequently released proteins) from adsorbent with the ligand 1.6-diamino hexane (coupled to 4% agarose)

Lane 6=Flow through (non-bound proteins) from load of adsorbent with the ligand diamino propane (coupled to 4% agarose)

Lane 7=Eluate (Bound and subsequently released proteins) from adsorbent with the ligand diamino propane (coupled to 4% agarose)

Lane 8=Flow through (non-bound proteins) from load of adsorbent with the ligand diamino octane (coupled to 6% agarose)

Lane 9=Eluate (Bound and subsequently released proteins) from adsorbent with the ligand diamino octane (coupled to 6% agarose)

Figure 10A:
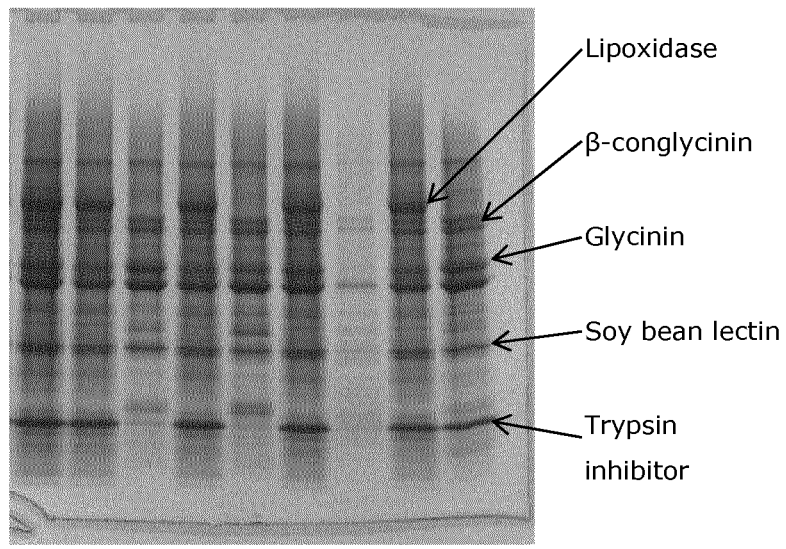
Figure 10B:
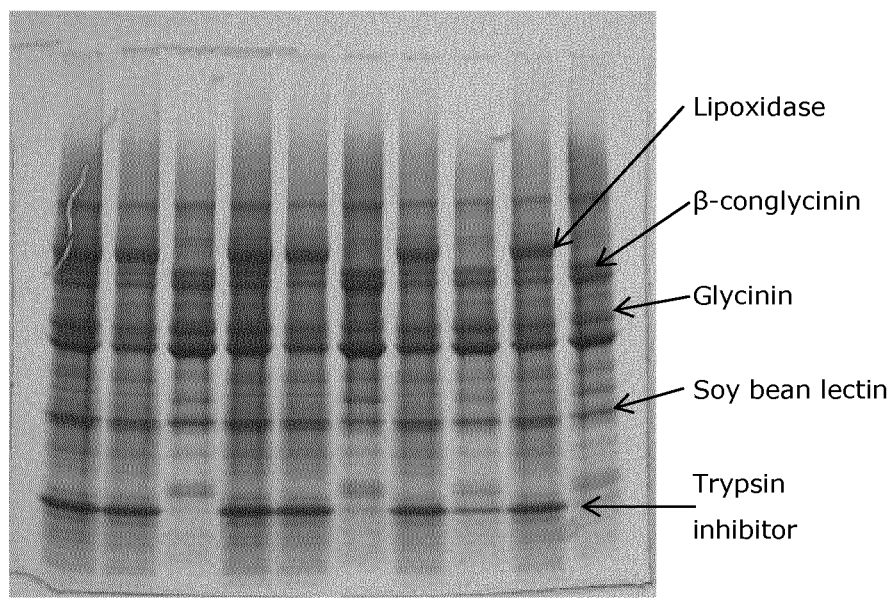
Figure 10C:
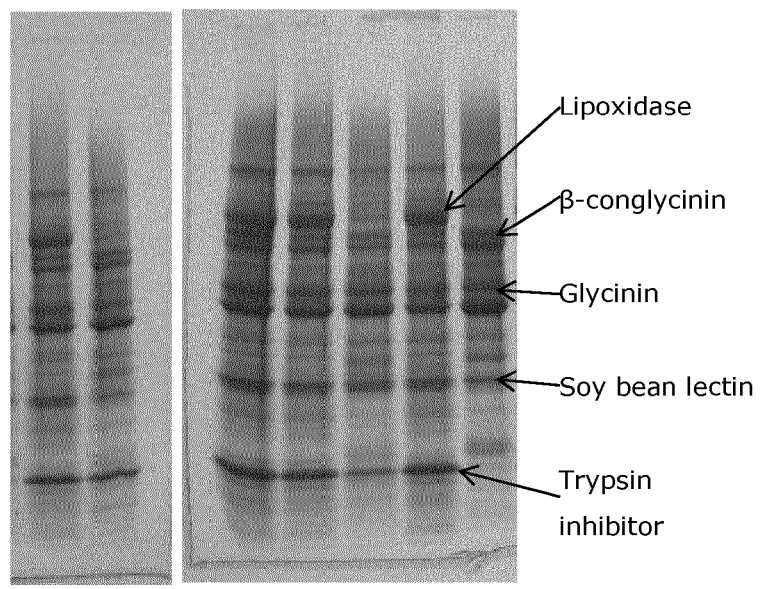
Figure 10D:
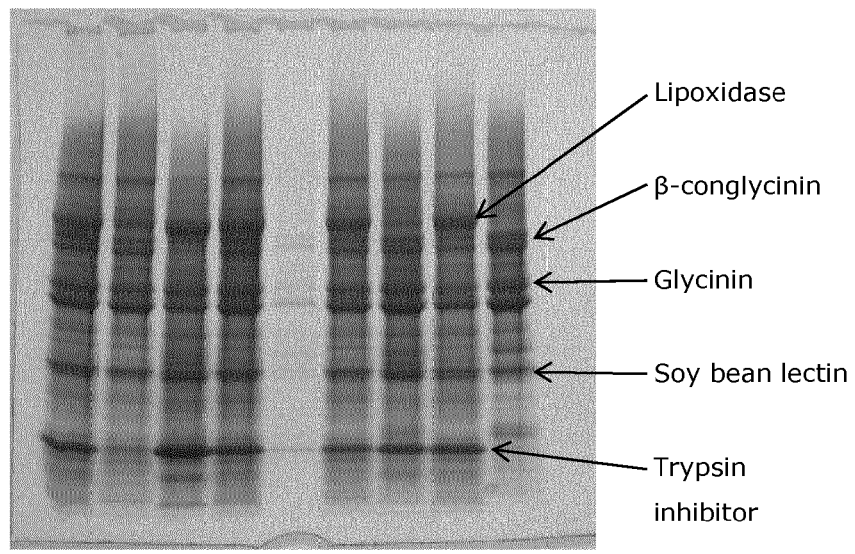
Figure 11A:
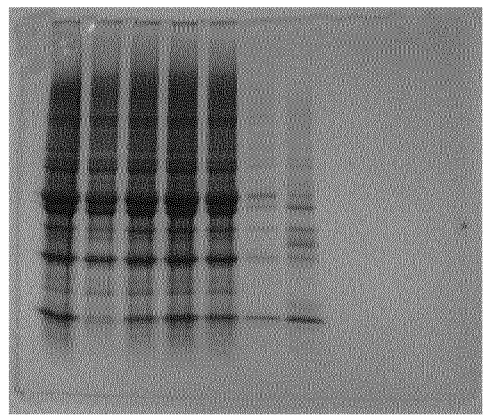
Figure 11B:
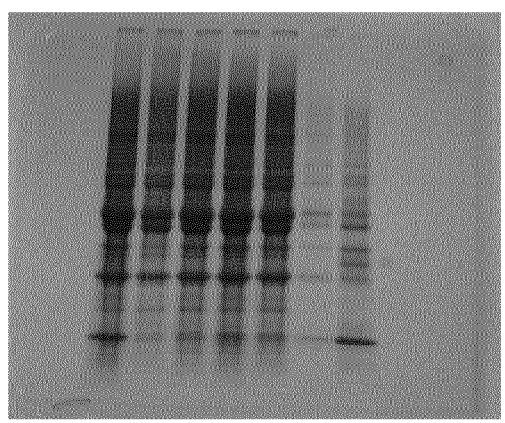
Figure 11C:
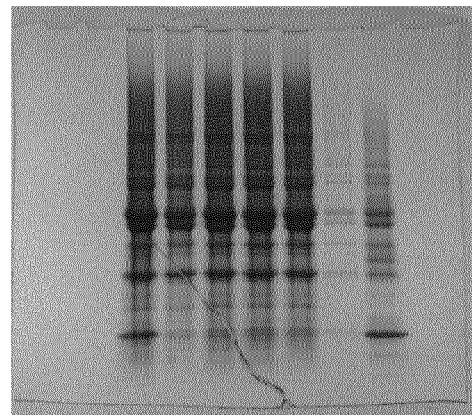
Figure 11D:
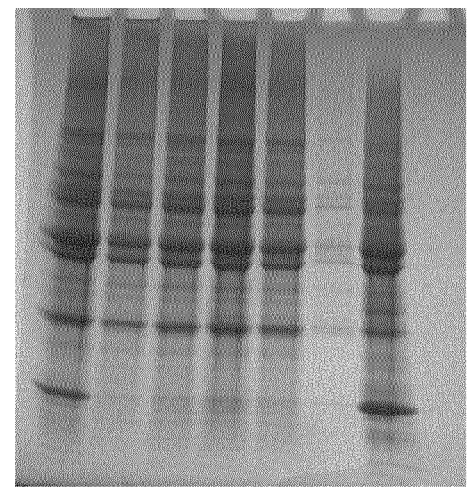
Figure 11E:
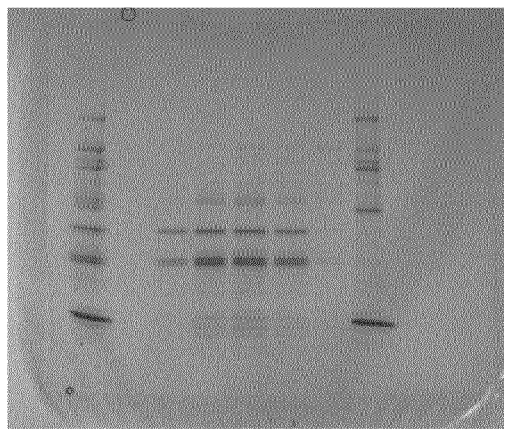
Figure 11F:
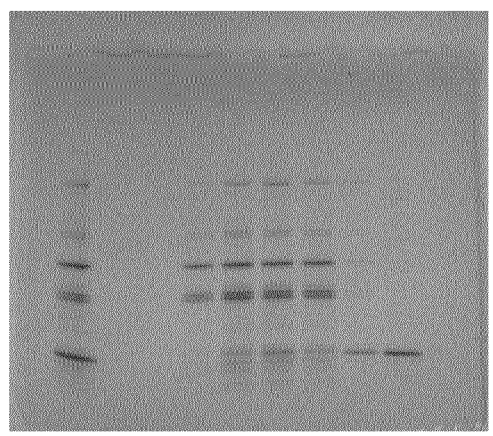

FIG. 10b for Example 12

Lane 10=soy extract at pH 6.0

Lane 11=Flow through (non-bound proteins) from load of adsorbent with the ligand N,N-di-methyl-di-aminopropane (coupled to 6% agarose)

Lane 12=Eluate (Bound and subsequently released proteins) from adsorbent with the ligand N,N-di-methyl-di-aminopropane (coupled to 6% agarose)

Lane 13=soy extract at pH 6.0

Lane 14=Flow through (non-bound proteins) from load of adsorbent with the ligand Pentylamine (coupled to 6% agarose)

Lane 15=Eluate (Bound and subsequently released proteins) from adsorbent with the ligand Pentylamine (coupled to 6% agarose)

Lane 16=Flow through (non-bound proteins) from load of adsorbent with the ligand 1,9-di-aminononane (coupled to 6% agarose)

Lane 17=Eluate (Bound and subsequently released proteins) from adsorbent with the ligand 1,9-di-aminonane (coupled to 6% agarose)

Lane 18=Flow through (non-bound proteins) from load of adsorbent with the ligand Di-butylamine (coupled to 6% agarose)

Lane 19=Eluate (Bound and subsequently released proteins) from adsorbent with the ligand Di-butylamine (coupled to 6% agarose)

FIG. 10c

Lane 20=Flow through (non-bound proteins) from load of adsorbent with the ligand Di-aminododecane (coupled to 5% agarose)

Lane 21=Eluate (Bound and subsequently released proteins) from adsorbent with the ligand Di-aminododecane (coupled to 5% agarose)

Lane 22=soy extract at pH 6.0

Lane 23=Flow through (non-bound proteins) from load of adsorbent with the ligand 2-aminobenzylamine (coupled to 6% agarose)

Lane 24=Eluate (Bound and subsequently released proteins) from adsorbent with the ligand 2-aminobenzylamine (coupled to 6% agarose)

Lane 25=Flow through (non-bound proteins) from load of adsorbent with the ligand Neopentylamine (coupled to 6% agarose)

Lane 26=Eluate (Bound and subsequently released proteins) from adsorbent with the ligand Neopentylamine (coupled to 6% agarose)

FIG. 10d

Lane 27=soy extract at pH 6.0

Lane 28=Flow through (non-bound proteins) from load of adsorbent with the ligand 2-aminobenzimidazole (coupled to 6% agarose)

Lane 29=Eluate (Bound and subsequently released proteins) from adsorbent with the ligand 2-aminobenzimidazole (coupled to 6% agarose)

Lane 30=Flow through (non-bound proteins) from load of adsorbent with the ligand 2,4-di-amino-6-hydroxypyrimidine (coupled to 6% agarose)

Lane 31=Eluate (Bound and subsequently released proteins) from adsorbent with the ligand 2,4-di-amino-6-hydroxypyrimidine (coupled to 6% agarose)

Lane 32=Flow through (non-bound proteins) from load of adsorbent with the ligand 2-aminobenzimidazole (coupled to 4% agarose)

Lane 33=Eluate (Bound and subsequently released proteins) from adsorbent with the ligand 2-aminobenzimidazole (coupled to 4% agarose)

Lane 34=Flow through (non-bound proteins) from load of adsorbent with the ligand 2-aminoimidazole (coupled to 6% agarose)

Lane 35=Eluate (Bound and subsequently released proteins) from adsorbent with the ligand 2-aminoimidazole (coupled to 6% agarose)

Example 13

Adsorbent coupled with the ligand hexylamine produced according to EXAMPLE 1, (the ligand concentration was determined with titration to be 31 mmol/L adsorbent) was tested for the ability to bind the trypsin inhibitor and other soy bean proteins at different pH-values: pH 9, pH 8, pH 7, pH 6, pH 5 and pH 4.5.

Procedure

Column preparation and flow rate as per Example 4. After packing the adsorbent was equilibrated with 10 ml 10 mM sodium citrate pH 4.5 respectively 10 mM sodium citrate pH 5.0, 10 mM sodium citrate pH 6.0, 10 mM di-potassium hydrogen phosphate pH 7.0, 10 mM tris pH 8.0 and 10 mM di-potassium hydrogen phosphate pH 9.0. The soy extract (produced at pH 9 according to EXAMPLE 2) was pH-adjusted with 1 M HCl to respectively pH 9.0, 8.0, 7.0, 6.0, 5.0 and 4.5 and centrifuged at 10,000 RPM to remove precipitated and non-soluble material. 7.5 ml of the centrifuged extract was loaded onto the column. The flow through (non-bound proteins) was collected in three 2.5 ml fractions. The column was then washed with 5 ml of deionized water. The flow through (non-bound and loosely bound proteins) was collected in one 5 ml fraction.

The bound proteins were subsequently released from the column (eluted) by applying 10 ml 50 mM NaOH. The flow through (eluted proteins, eluate) was collected in one 10 ml fraction and pH in the eluate fraction was immediately adjusted to pH 7.0 by addition of 1 M The performance of the adsorbent was determined by SDS-PAGE (as described in EXAMPLE 3). See FIGS. 11a-f.

The results indicate that at pH 9.0 only a small amount of protein is bound to the adsorbent (see lane 7 representing the eluate fraction containing only a few very weak bands. Lane 1 representing the bands from all the proteins in the soy extract and lane 2-5 representing the bands of non-bound proteins in the flow through fractions. The intensity of these bands are very similar to the bands in lane 1, meaning that the adsorbent does not bind these proteins). Only a minor fraction of the trypsin inhibitor is bound and released into the eluate (see lane 7).

At pH 8.0 most of the trypsin inhibitor is bound to the adsorbent and a fraction of the other soy bean proteins (see lane 9 to 11 representing the flow-through fractions containing non-bound proteins are practically devoid of the trypsin inhibitor band, a weak trypsin inhibitor band starts to appear in the last flow through fraction=lane 11). The trypsin inhibitor and other proteins bound to the adsorbent is recovered in the eluate (see lane 14).

At pH 7.0, pH 6.0 and pH 5.0 all the trypsin inhibitor is bound to the adsorbent and a fraction of the other soy bean proteins. The trypsin inhibitor is recovered together with other bound proteins in the eluate (see respectively lane 21, lane 28 and lane 35. The flow through fractions from the loading of the adsorbent from these three pH-values does not contain the trypsin inhibitor (see respectively lane 19, lane 26 and lane 33).

At pH 4.5 it is practically only the trypsin inhibitor that is bound to the adsorbent, a fraction of the trypsin inhibitor does not bind (see lane 38 and 39 representing the last two run-through fractions from the loading of the adsorbent and lane 41 representing the wash weak bands of trypsin inhibitor is detected meaning that it does not bind to the adsorbent). The trypsin inhibitor is recovered in the eluate (see lane 42, very few other bands than the band representing the trypsin inhibitor is detected).

In the table below the purity of the trypsin inhibitor (TI) in the eluate at the different pH-values tested is calculated by scanning densitometry performed on the SDS-PAGE gels. An image processing system is used for the scanning of the different lanes (Alphalmanager gel documentation system from Alpha Innotech, (Protein Simple, USA)).

| pH | TI purity in eluate, % |
|---|---|
| 9 | 24.0 |
| 8 | 32.6 |
| 7 | 21.9 |
| 6 | 26.9 |
| 5 | 38.1 |
| 4.5 | 72.0 |

Using the same principle it was estimated that the relative content of trypsin inhibitor per gram of protein was reduced from the starting material to the total run through fraction (the non-bound protein fraction) according to the table below.

| pH | Starting material | Total run through fraction. Trypsin inhibitor concentration/g protein |
|---|---|---|
| 9.0 | 100% | 30% |
| 8.0 | 100% | 15% |
| 7.0 | 100% | 10% |
| 6.0 | 100% | <2% |
| 5.0 | 100% | <2% |
| 4.5 | 100% | <2% |

FIGS. 11a-11f:
Lane 1=soy extract at pH 9.0
Lane 2=Flow through fraction 1 (non-bound proteins) from load of adsorbent with the ligand Hexylamine, pH 9.0
Lane 3=Flow through fraction 2 (non-bound proteins) from load of adsorbent with the ligand Hexylamine, pH 9.0
Lane 4=Flow through fraction 3 (non-bound proteins) from load of adsorbent with the ligand Hexylamine, pH 9.0
Lane 5=Flow through pool of fraction 1 to 3 (non-bound proteins) from load of adsorbent with the ligand Hexylamine, pH 9.0
Lane 6=Wash (non-bound and loosely bound proteins) of the adsorbent with the ligand Hexylamine
Lane 7=Eluate (Bound and subsequently released proteins) from adsorbent with the ligand Hexylamine (experiment performed at pH 9.0)
Lane 8=soy extract at pH 8.0
Lane 9=Flow through fraction 1 (non-bound proteins) from load of adsorbent with the ligand Hexylamine, pH 8.0
Lane 10=Flow through fraction 2 (non-bound proteins) from load of adsorbent with the ligand Hexylamine, pH 8.0
Lane 11=Flow through fraction 3 (non-bound proteins) from load of adsorbent with the ligand Hexylamine, pH 8.0
Lane 12=Flow through pool of fraction 1 to 3 (non-bound proteins) from load of adsorbent with the ligand Hexylamine, pH 8.0
Lane 13=Wash (non-bound and loosely bound proteins) of the adsorbent with the ligand Hexylamine
Lane 14=Eluate (Bound and subsequently released proteins) from adsorbent with the ligand Hexylamine (experiment performed at pH 8.0)
Lane 15=soy extract at pH 7.0
Lane 16=Flow through fraction 1 (non-bound proteins) from load of adsorbent with the ligand Hexylamine, pH 7.0
Lane 17=Flow through fraction 2 (non-bound proteins) from load of adsorbent with the ligand Hexylamine, pH 7.0
Lane 18=Flow through fraction 3 (non-bound proteins) from load of adsorbent with the ligand Hexylamine, pH 7.0
Lane 19=Flow through pool of fraction 1 to 3 (non-bound proteins) from load of adsorbent with the ligand Hexylamine, pH 7.0
Lane 20=Wash (non-bound and loosely bound proteins) of the adsorbent with the ligand Hexylamine
Lane 21=Eluate (Bound and subsequently released proteins) from adsorbent with the ligand Hexylamine (experiment performed at pH 7.0)
Lane 22=soy extract at pH 6.0
Lane 23=Flow through fraction 1 (non-bound proteins) from load of adsorbent with the ligand Hexylamine, pH 6.0
Lane 24=Flow through fraction 2 (non-bound proteins) from load of adsorbent with the ligand Hexylamine, pH 6.0
Lane 25=Flow through fraction 3 (non-bound proteins) from load of adsorbent with the ligand Hexylamine, pH 6.0
Lane 26=Flow through pool of fraction 1 to 3 (non-bound proteins) from load of adsorbent with the ligand Hexylamine, pH 6.0
Lane 27=Wash (non-bound and loosely bound proteins) of the adsorbent with the ligand Hexylamine
Lane 28=Eluate (Bound and subsequently released proteins) from adsorbent with the ligand Hexylamine (experiment performed at pH 6.0)
Lane 29=soy extract at pH 5.0
Lane 30=Flow through fraction 1 (non-bound proteins) from load of adsorbent with the ligand Hexylamine, pH 5.0
Lane 31=Flow through fraction 2 (non-bound proteins) from load of adsorbent with the ligand Hexylamine, pH 5.0
Lane 32=Flow through fraction 3 (non-bound proteins) from load of adsorbent with the ligand Hexylamine, pH 5.0
Lane 33=Flow through pool of fraction 1 to 3 (non-bound proteins) from load of adsorbent with the ligand Hexylamine, pH 5.0
Lane 34=Wash (non-bound and loosely bound proteins) of the adsorbent with the ligand Hexylamine Lane 35=Eluate (Bound and subsequently released proteins) from adsorbent with the ligand Hexylamine (experiment performed at pH 5.0)

Lane 36=soy extract at pH 4.5

Lane 30=Flow through fraction 1 (non-bound proteins) from load of adsorbent with the ligand Hexylamine, pH 4.5

Lane 37=Flow through fraction 2 (non-bound proteins) from load of adsorbent with the ligand Hexylamine, pH 4.5

Lane 38=Flow through fraction 3 (non-bound proteins) from load of adsorbent with the ligand Hexylamine, pH 4.5

Lane 39=Flow through pool of fraction 1 to 3 (non-bound proteins) from load of adsorbent with the ligand Hexylamine, pH 4.5

Lane 40=Wash (non-bound and loosely bound proteins) of the adsorbent with the ligand Hexylamine Lane 41=Eluate (Bound and subsequently released proteins) from adsorbent with the ligand Hexylamine (experiment performed at pH 4.5)

Example 14

Adsorbent coupled with the ligand benzylamine produced according to EXAMPLE 1, (the ligand concentration was determined with titration to be 55 mmol/L adsorbent) was tested for the ability to bind the trypsin inhibitor and other soy bean proteins at different pH-values: pH 9, pH 8, pH 7, pH 6, pH 5 and pH 4.5.

Procedure

Column preparation and flow rate as per Example 4. After packing the adsorbent was equilibrated with 10 ml 10 mM sodium citrate pH 4.5 respectively 10 mM sodium citrate pH 5.0, 10 mM sodium citrate pH 6.0, 10 mM di-potassium hydrogen phosphate pH 7.0, 10 mM tris pH 8.0 and 10 mM di-potassium hydrogen phosphate pH 9.0. The soy extract (produced at pH 9 according to EXAMPLE 2) was pH-adjusted with 1 M HCl to respectively pH 9.0, 8.0, 7.0, 6.0, 5.0 and 4.5 and centrifuged at 10,000 RPM to remove precipitated and non-soluble material. 7.5 ml of the centrifuged extract was loaded onto the column. The flow through (non-bound proteins) was collected in one 7.5 ml fraction. The column was then washed with 5 ml of deionized water. The flow through (non-bound and loosely bound proteins) was collected in one fraction.

The bound proteins were subsequently released from the column (eluted) by applying 10 ml 50 mM NaOH. The flow through (eluted proteins, eluate) was collected in one fraction and pH in the eluate fraction was immediately adjusted to pH 7.0 by addition of 1 M The performance of the adsorbent was determined by SDS-PAGE (performed as described in EXAMPLE 3). See FIG. 12.

The results indicate that at pH 9 only a small amount of protein is bound to the adsorbent (see lane 3 representing the eluate fraction containing only a few very weak bands. Lane 1 representing the bands from all the proteins in the soy extract and lane 2 representing the bands of non-bound proteins in the flow through fraction. The intensity of these bands are very similar to the bands in lane 1 meaning that the adsorbent does not bind these proteins).

At pH 8 all the trypsin inhibitor is bound to the adsorbent and a small fraction of the other soy bean proteins (see lane 5 representing the run-through fraction containing non-bound proteins is practically devoid of the trypsin inhibitor band, bands representing all the other proteins are still there and the intensity of these bands are very similar the bands in lane 5=soy bean extract meaning that the adsorbent does not bind these proteins). The trypsin inhibitor is recovered in the eluate (see lane 6).

At pH 7 all the trypsin inhibitor is bound to the adsorbent and a fraction of the other soy bean proteins. At pH 7 more other proteins bind to the adsorbent than at pH 8 (see lane 8 representing the run-through fraction containing non-bound proteins is practically devoid of the trypsin inhibitor band. The trypsin inhibitor is recovered together with other bound proteins in the eluate (see lane 9. Comparing lane 6=eluate from pH 8.0 with lane 9=eluate from pH 7.0 the trypsin inhibitor bands are very similar in intensity, but the bands representing the other proteins have a stronger intensity for pH 7.0 than 8.0 meaning that more other proteins have bound at pH 7.0).

At pH 6 all the trypsin inhibitor is bound to the adsorbent and a fraction of the other soy bean proteins (see lane 11 representing the run-through fraction containing non-bound proteins is practically devoid of the trypsin inhibitor band). The trypsin inhibitor is recovered together with other bound proteins in the eluate (see lane 12).

At pH 5 all the trypsin inhibitor is bound to the adsorbent and a fraction of the other soy bean proteins (see lane 14 representing the run-through fraction containing non-bound proteins is practically devoid of the trypsin inhibitor band). The trypsin inhibitor is recovered together with other bound proteins in the eluate (see lane 15).

At pH 4.5 all the trypsin inhibitor is bound to the adsorbent and a fraction of the other soy bean proteins (see lane 17 representing the run-through fraction containing non-bound proteins is practically devoid of the trypsin inhibitor band). The trypsin inhibitor is recovered together with other bound proteins in the eluate (see lane 18).

In the table below the purity of the trypsin inhibitor (TI) in the eluate at different pH-values tested is calculated by scanning densitometry performed on the SDS-PAGE gels. An image processing system is used for the scanning of the different lanes (Alphalmanager gel documentation system from Alpha Innotech, (Protein Simple, USA))

| pH | TI purity in eluate, % |
|---|---|
| 9 | 36.9 |
| 8 | 36.6 |
| 7 | 36.0 |
| 6 | 30.9 |
| 5 | 31.1 |
| 4.5 | 46.0 |

Using the same principles it was estimated that the total run through fraction (non-bound proteins) at pH 6.0 contained less than 10% of the trypsin inhibitor protein per gram of total protein compared to the starting material.

Figure 12:
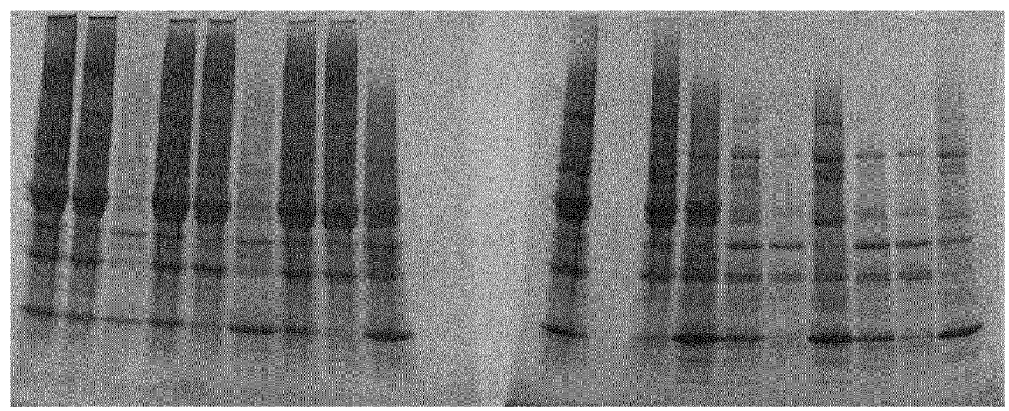
Figure 13:
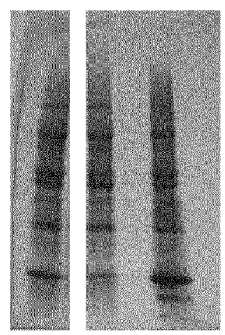
Figure 14:
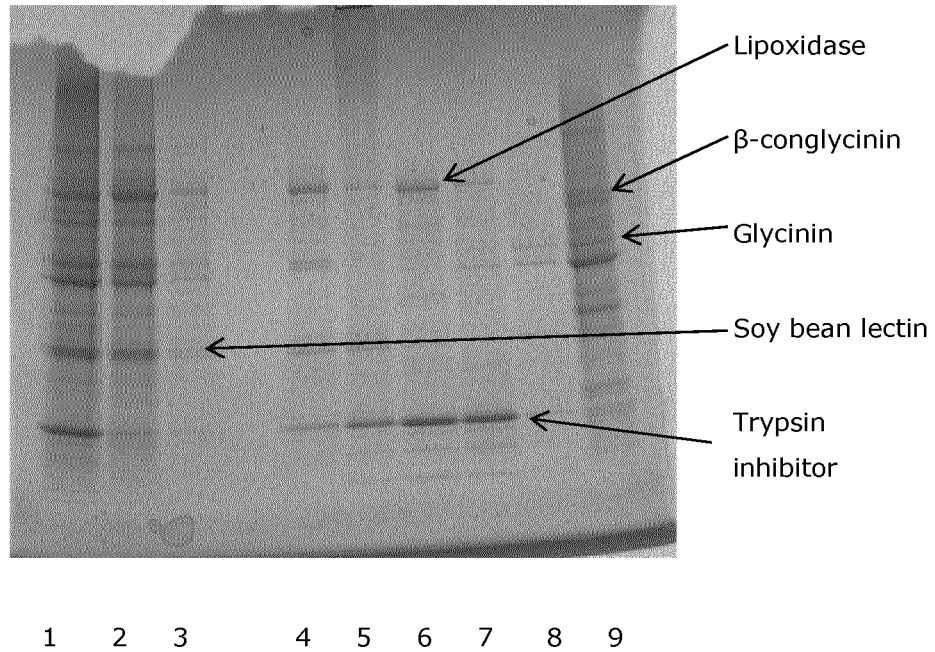
Figure 15:
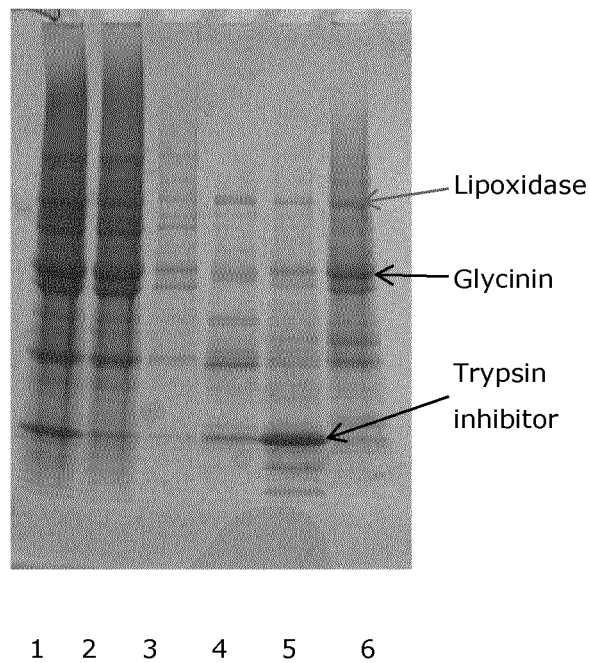
Figure 16A:
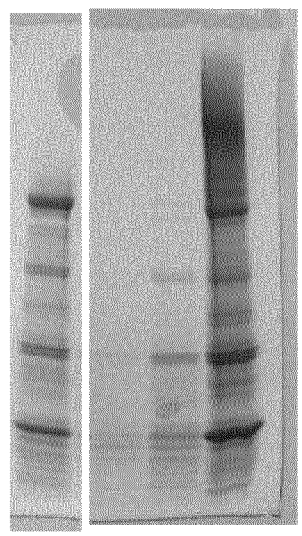
Figure 16B:
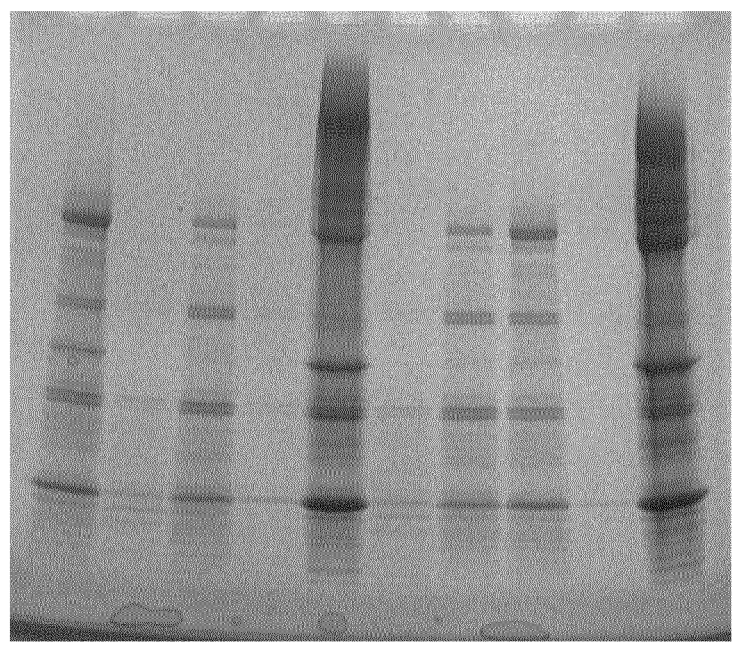
Figure 19A:
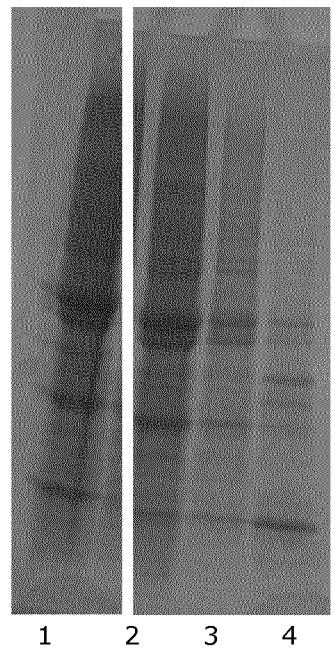
Figure 19B:
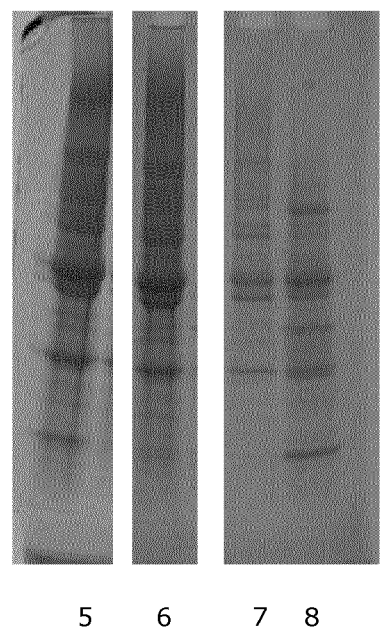
Figure 19C:
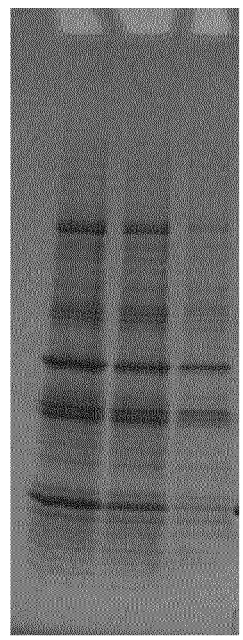

FIG. 12 for Example 14

Lane 1=soy extract at pH 9.0

Lane 2=Flow through (non-bound proteins) from load of adsorbent with the ligand Benzylamine, pH 9.0

Lane 3=Eluate (Bound and subsequently released proteins) from adsorbent with the ligand Benzylamine (experiment performed at pH 9.0)

Lane 4=soy extract at pH 8.0

Lane 5=Flow through (non-bound proteins) from load of adsorbent with the ligand Benzylamine, pH 8.0

Lane 6=Eluate (Bound and subsequently released proteins) from adsorbent with the ligand Benzylamine (experiment performed at pH 8.0)

Lane 7=soy extract at pH 7.0
Lane 8=Flow through (non-bound proteins) from load of adsorbent with the ligand Benzylamine, pH 7.0
Lane 9=Eluate (Bound and subsequently released proteins) from adsorbent with the ligand Benzylamine (experiment performed at pH 7.0)
Lane 10=soy extract at pH 6.0
Lane 11=Flow through (non-bound proteins) from load of adsorbent with the ligand Benzylamine, pH 6.0
Lane 12=Eluate (Bound and subsequently released proteins) from adsorbent with the ligand Benzylamine (experiment performed at pH 12.0)
Lane 13=soy extract at pH 5.0
Lane 14=Flow through (non-bound proteins) from load of adsorbent with the ligand Benzylamine, pH 5.0
Lane 15=Eluate (Bound and subsequently released proteins) from adsorbent with the ligand Benzylamine (experiment performed at pH 5.0)
Lane 16=soy extract at pH 4.5
Lane 17=Flow through (non-bound proteins) from load of adsorbent with the ligand Benzylamine, pH 4.5
Lane 18=Eluate (Bound and subsequently released proteins) from adsorbent with the ligand Benzylamine (experiment performed at pH 4.5)

Example 15

Adsorbent coupled with the ligand hexylamine produced according to EXAMPLE 1, (the ligand concentration was determined with titration to be 31 mmol/L adsorbent) was loaded with soy bean proteins at pH 6, and was eluted with a dilute alkali solution in order to achieve a resulting protein solution (eluate) with low ionic strength in order to facilitate further down stream processing. Because of the low conductivity no diafiltration was needed during the ultrafiltration of the product before it was dried.

Two experiments were performed where the elution of the bound proteins was performed with respectively 50 mM NaOH (11.5 mS/cm) and 10 mM NaOH (2.4 mS/cm)

Procedure

Column preparation and flow rate as per Example 4. After packing the adsorbent was equilibrated with 10 ml 10 mM sodium citrate pH 6.0. The soy extract (produced at near neutral pH according to EXAMPLE 2) was pH-adjusted with 1 M HCl to pH 6.0 and centrifuged at 10,000 RPM to remove precipitated and non-soluble material. 7.5 ml of the centrifuged extract was loaded onto the column. The flow through (non-bound proteins) was collected in one 7.5 ml fraction. The column was then washed with 5 ml of deionized water. The flow through (non-bound and loosely bound proteins) was collected in one 5 ml fraction.

The bound proteins were subsequently released from the column (eluted) by applying 10 ml 10 mM NaOH respectively 10 ml 50 mM NaOH. The flow through (eluted proteins, eluate) was collected in one 10 ml fraction and pH in the eluate fraction was immediately adjusted to pH 7.0 by addition of 1 M HCl. Dry matter determination was performed on the two eluates according to EXAMPLE 3.

The resulting conductivity in the eluate from the 10 mM NaOH elution buffer was 591 µS/cm. The dry matter determination shows a yield of 44 mg protein in the eluate corresponding to 5.9 mg protein per ml soy extract loaded onto the column.

The resulting conductivity in the eluate from the 50 mM NaOH elution buffer was 4.95 mS/cm in eluate. The dry matter determination shows a yield of 41 mg protein in the eluate corresponding to 5.5 mg protein per ml soy extract loaded onto the column.

The results indicate that the bound proteins on the adsorbent coupled with the ligand hexylamine can be eluted with a dilute sodium hydroxide solution resulting in a protein solution (eluate) with low ionic strength. Due to the low conductivity, no diafiltration was needed during the ultrafiltration of the product before it was dried.

Example 16

An adsorbent with the ligand benzylamine produced according to EXAMPLE 1, (the ligand concentration was determined with titration to be 55 mmol/L adsorbent) was used for isolation of trypsin inhibitor from a soy bean extract.

Procedure

Column preparation and flow rate as per Example 4. After packing the adsorbent was equilibrated with 10 ml 10 mM sodium citrate pH 6.0. The soy extract (produced at near neutral pH according to EXAMPLE 2) was pH-adjusted with 1 M HCl to pH 6.0 and centrifuged at 10,000 RPM to remove precipitated and non-soluble material. 20 ml of the centrifuged extract was loaded onto the column. The flow through (non-bound proteins) was collected in one fraction. The column was then washed with 5 ml of deionized water. The flow through (non-bound and loosely bound proteins) was collected in one fraction.

The bound proteins were subsequently released from the column (eluted) by applying 10 ml 50 mM NaOH. The flow through (eluted proteins, eluate) was collected in one fraction and pH in the eluate fraction was immediately adjusted to pH 7.0 by addition of 1 M The amount of protein bound to the adsorbent was determined with dry matter determination as described in EXAMPLE 3. The dry matter determination shows a yield of 60 mg protein in the eluate corresponding to 3 mg protein per ml soy extract loaded onto the column.

The performance of the adsorbent was determined by SDS-PAGE (as described in EXAMPLE 3). See FIG. 13.

The results indicate that most of the trypsin inhibitor is bound to the adsorbent and a small fraction of the other soy bean proteins (see lane 2 representing the run-through fraction containing non-bound proteins is low in trypsin inhibitor content (low intensity of the trypsin inhibitor band), bands representing all the other proteins are still there and the intensity of these bands are very similar to the bands in lane 1=soy bean extract, meaning that the adsorbent does not bind these proteins). The trypsin inhibitor is recovered in the eluate (see lane 4).

Lane 1=soy extract at pH 6.0
Lane 2=Flow through (non-bound proteins) from load of adsorbent with the ligand Benzylamine at pH 6.0.
Lane 3=Wash (non-bound and loosely bound proteins) of the adsorbent with the ligand Benzylamine
Lane 4=Eluate (Bound and subsequently released proteins) from adsorbent with the ligand Benzylamine Example 17

The example shows how the trypsin inhibitor was eluted selectively from an adsorbent coupled with the ligand Hexylamine (Produced as described in EXAMPLE 1), (the ligand concentration was determined with titration to be 31 mmol/L adsorbent) where the proteins have been bound at pH 6.0. During elution the pH was step wise decreased by applying dilute buffers with decreasing pH values.

Procedure

Column preparation and flow rate as per Example 4. After packing the adsorbent was equilibrated with 10 ml 10 mM sodium citrate pH 6.0. The soy extract (produced at near neutral pH according to EXAMPLE 2) was pH-adjusted with 1 M HCl to 6.0. The extract was centrifuged at 10,000 RPM to remove non-soluble and precipitated material. 7.5 ml of the centrifuged extract was loaded onto the column. The flow through (non-bound proteins) was collected in one fraction of 7.5 ml. The adsorbent was washed with 5 ml of deionized water. The flow through (non-bound and loosely bound proteins) was collected in one 5 ml fraction.

The bound proteins were subsequently released from the column (eluted) by applying the following buffers:

10 mM sodium citrate pH 5.75, 10 ml, the flow through (eluted proteins, eluate) was collected in one 10 ml fraction.

10 mM sodium citrate pH 4.5, 10 ml, the flow through (eluted proteins, eluate) was collected in one 10 ml fraction.

10 mM sodium citrate pH 4.0, 10 ml, the flow through (eluted proteins, eluate) was collected in one 10 ml fraction.

10 mM sodium citrate pH 3.5, 10 ml, the flow through (eluted proteins, eluate) was collected in one 10 ml fraction.

10 mM sodium citrate pH 3.0, 10 ml, the flow through (eluted proteins, eluate) was collected in one 10 ml fraction.

50 mM NaOH, 10 ml, the flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIG. 14. Arrows indicate bands identified in EXAMPLE 3 using purified soy proteins.

The results indicate that the adsorbent bound essentially all the trypsin inhibitor applied to the column and a minor fraction of the other proteins (see lane 2 representing the run-through fraction containing non-bound proteins is practically devoid of the trypsin inhibitor band, bands representing all the other proteins are still there and the intensity of these bands are very similar to the bands in lane 1=soy bean extract meaning that the adsorbent does not bind these proteins).

The trypsin inhibitor was eluted in the pH-range of 5.75 to 3.5 (see lane 4-7) from the Hexylamine ligand before most other proteins were eluted by 50 mM NaOH solution (see lane 9).

Lane 1=soy extract at pH 6.0
Lane 2=Flow through (non-bound proteins) from load of adsorbent with the ligand Hexylamine at pH 6.0.
Lane 3=Wash (non-bound and loosely bound proteins) of the adsorbent with the ligand Hexylamine
Lane 4=Eluate (Bound and subsequently released proteins) from adsorbent with the ligand Hexylamine at pH 5.75
Lane 5=Eluate (Bound and subsequently released proteins) from adsorbent with the ligand Hexylamine at pH 4.5
Lane 6=Eluate (Bound and subsequently released proteins) from adsorbent with the ligand Hexylamine at pH 4.0
Lane 7=Eluate (Bound and subsequently released proteins) from adsorbent with the ligand Hexylamine at pH 3.5
Lane 8=Eluate (Bound and subsequently released proteins) from adsorbent with the ligand Hexylamine at pH 3.0
Lane 9=Eluate (Bound and subsequently released proteins) from adsorbent with the ligand Hexylamine with 50 mM NaOH Example 18

The example shows how the trypsin inhibitor was eluted selectively from an adsorbent coupled with the ligand Benzylamine (Produced as described in EXAMPLE 1), (the ligand concentration was determined with titration to be 55 mmol/L adsorbent) where the proteins have been bound at pH 6.0. During elution the pH was step decreased to respectively a) 10 mM sodium citrate pH 4.5, b) 10 mM sodium citrate pH 3.0 and c) 50 mM NaOH.

Procedure

Column preparation and flow rate as per Example 4. After packing the adsorbent was equilibrated with 10 ml 10 mM sodium citrate pH 6.0. The soy extract (produced at near neutral pH according to EXAMPLE 2) was pH-adjusted with 1 M HCl to 6.0. The extract was centrifuged at 10,000 RPM to remove non-soluble and precipitated material. 7.5 ml of the centrifuged extract was loaded onto the column. The flow through (non-bound proteins) was collected in one fraction of 7.5 ml. The adsorbent was washed with 5 ml of deionized water. The flow through (non-bound and loosely bound proteins) was collected in one 5 ml fraction.

The bound proteins were subsequently released from the column (eluted) by applying the following buffers:

a) 10 mM sodium citrate pH 4.5, 10 ml, the flow through (eluted proteins, eluate) was collected in one 10 ml fraction.
b) 10 mM sodium citrate pH 3.0, 10 ml, the flow through (eluted proteins, eluate) was collected in one 10 ml fraction.
c) 50 mM NaOH, 10 ml, the flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIG. 15. Arrows indicate bands identified in EXAMPLE 3 using purified soy proteins.

The results indicate that the adsorbent bound essentially all the trypsin inhibitor applied to the column and a minor fraction of the other proteins (see lane 2 representing the run-through fraction containing non-bound proteins is practically devoid of the trypsin inhibitor band).

The trypsin inhibitor was eluted at pH 3.0 (see lane 5) from the Benzylamine ligand. Other proteins were eluted by respectively pH 4.5 and 50 mM NaOH solution (see lane 4 and 6).

Figure Y for Example 18
Lane 1=soy extract at pH 6.0
Lane 2=Flow through (non-bound proteins) from load of adsorbent with the ligand Benzylamine at pH 6.0.
Lane 3=Wash (non-bound and loosely bound proteins) of the adsorbent with the ligand Benzylamine
Lane 4=Eluate (Bound and subsequently released proteins) from adsorbent with the ligand Benzylamine at pH 4.5
Lane 5=Eluate (Bound and subsequently released proteins) from adsorbent with the ligand Benzylamine at pH 3.0
Lane 6=Eluate (Bound and subsequently released proteins) from adsorbent with the ligand Benzylamine with 50 mM NaOH

Example 19

The example shows the amount of soy protein that was recovered in the eluate from an adsorbent coupled with the ligand 4-aminobenzoic acid (Produced as described in EXAMPLE 1), (the ligand concentration was determined with titration to be 30 mmol/L adsorbent) where the load ratio was respectively 1:10 (10 L extract loaded per liter of adsorbent), 1:20 and 1:30 at pH 4.5. The amount of bound protein was determine with dry matter determination as described in EXAMPLE 3

Procedure

Column preparation and flow rate as per Example 4. After packing the adsorbent was equilibrated with 10 ml 10 mM sodium citrate pH 4.5. The soy extract (produced at near neutral pH according to EXAMPLE 2) was pH-adjusted with 1 M HCl to pH 4.5. The extract was centrifuged at 10,000 RPM to remove non-soluble and precipitated material. Respectively 10 ml, 20 ml and 30 ml of the centrifuged extract was loaded onto the column. The flow through (non-bound proteins) was collected in 10 ml fractions. The adsorbent was washed with 5 ml of deionized water. The flow through (non-bound and loosely bound proteins) was collected in one 5 ml fraction.

The bound proteins were subsequently released from the column (eluted) by applying 10 ml 50 mM NaOH. The flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIGS. 16a and 16b.

The table shows the amount of protein eluted from the column with the different load ratios (determined with dry matter determination as described in EXAMPLE 3). The adsorbent binding capacity is calculated as mg protein in the eluate divided by the adsorbent volume (1 ml). The yield is calculated as mg protein in the eluate divided by the extract load volume (10, respectively 20 and 30 ml).

| Load ratio | mg protein in eluate | Adsorbent binding capacity, mg protein/ml adsorbent | Yield, mg protein/ml loaded extract |
|---|---|---|---|
| 1:10 | 33.0 | 33.0 | 3.3 |
| 1:20 | 45.3 | 45.3 | 2.3 |
| 1:30 | 55.0 | 55.0 | 1.8 |

The results indicate that the more soy bean extract loaded onto the adsorbent coupled with the ligand 4-aminobenzoic acid the higher binding capacity is achieved meaning a high yield of protein per purification cycle.

Lane 1=soy extract at pH 4.5
Lane 2=Flow through (non-bound proteins) from load of adsorbent with the ligand 4-aminobenzoic acid (4% agarose beads) at pH 4.5.
Lane 3=Wash (non-bound and loosely bound proteins) of the adsorbent with the ligand 4-aminobenzoic acid (4% agarose beads)
Lane 4=Eluate (Bound and subsequently released proteins) from adsorbent with the ligand 4-aminobenzoic acid (4% agarose beads)
Lane 5=soy extract at pH 4.5
Lane 6=Flow through fraction 1 (non-bound proteins) from load of adsorbent with the ligand 4-aminobenzoic acid (4% agarose beads) at pH 4.5.
Lane 7=Flow through fraction 2 (non-bound proteins) from load of adsorbent with the ligand 4-aminobenzoic acid (4% agarose beads) at pH 4.5.
Lane 8=Wash (non-bound and loosely bound proteins) of the adsorbent with the ligand 4-aminobenzoic acid (4% agarose beads)
Lane 9=Eluate (Bound and subsequently released proteins) from adsorbent with the ligand 4-aminobenzoic acid (4% agarose beads)
Lane 10=Flow through fraction 1 (non-bound proteins) from load of adsorbent with the ligand 4-aminobenzoic acid (4% agarose beads) at pH 4.5.
Lane 11=Flow through fraction 2 (non-bound proteins) from load of adsorbent with the ligand 4-aminobenzoic acid (4% agarose beads) at pH 4.5.
Lane 12=Flow through fraction 2 (non-bound proteins) from load of adsorbent with the ligand 4-aminobenzoic acid (4% agarose beads) at pH 4.5.
Lane 13=Wash (non-bound and loosely bound proteins) of the adsorbent with the ligand 4-aminobenzoic acid (4% agarose beads)
Lane 14=Eluate (Bound and subsequently released proteins) from adsorbent with the ligand 4-aminobenzoic acid (4% agarose beads)

Example 20

The example shows the amount of soy protein that was recovered in the eluate from an adsorbent coupled with the ligand 4-mercaptobenzoic acid (Produced as described in EXAMPLE 1), (the ligand concentration was determined with titration to be 51 mmol/L adsorbent) where the load ratio was 1:20 (20 L extract loaded per liter of adsorbent) at pH 4.5. The amount of protein was determine with dry matter determination as described in EXAMPLE 3

Procedure

Column preparation and flow rate as per Example 4. After packing the adsorbent was equilibrated with 10 ml 10 mM sodium citrate pH 4.5. The soy extract (produced at near neutral pH according to EXAMPLE 2) was pH-adjusted with 1 M HCl to pH 4.5. The extract was centrifuged at 10,000 RPM to remove non-soluble and precipitated material. 20 ml of the centrifuged extract was loaded onto the column. The flow through (non-bound proteins) was collected in one 20 ml fraction. The adsorbent was washed with 5 ml of deionized water. The flow through (non-bound and loosely bound proteins) was collected in one 5 ml fraction.

The bound proteins were subsequently released from the column (eluted) by applying 10 ml 50 mM NaOH. The flow through (eluted proteins, eluate) was collected in one 10 ml fraction and pH in the eluate fraction was immediately adjusted to pH 7.0 by addition of 1 M HCl.

The dry matter in the eluate was determine according to EXAMPLE 3. The result showed that in the eluate was recovered 57 mg protein which corresponds to 2.85 mg protein per ml soy extract. This results in an adsorbent binding capacity of 57 mg protein per ml adsorbent.

Example 21

The example shows how the trypsin inhibitor was eluted selectively from an adsorbent coupled with the ligand 4-aminobenzoic acid (Produced as described in EXAMPLE 1), (the ligand concentration was determined with titration to be 30 mmol/L adsorbent), where the proteins have been bound at pH 4.5. The trypsin inhibitor was selectively eluted with 10 mM sodium citrate pH 6.0 and the other bound proteins with 10 mM NaOH.

The experiment was performed with Expanded Bed Adsorption (EBA) chromatography.

EBA column used for the experiment: 1 cm diameter laboratory EBA column with a 150 cm glass tube (Cat. No.: 7010-0100+7010-1500, Upfront Chromatography A/S, Denmark)

Procedure

The column was packed with 50 cm settled bed height, equal to 40 ml adsorbent. Flow rate during load of extract: 10 cm/min=8 ml/min. Flow rate during equilibration, wash and elution: 15 cm/min=12 ml/min. After packing the adsorbent was equilibrated with 200 ml 10 mM sodium citrate pH 4.5. The soy extract (produced at near neutral pH according to EXAMPLE 2) was pH-adjusted with 1 M HCl to pH 4.5. The extract was loaded directly onto the column without centrifugation. 600 ml of the extract was loaded onto the column. The flow through (non-bound proteins) was collected in three 200 ml fractions. The adsorbent was washed with 230 ml of deionized water. The flow through (non-bound and loosely bound proteins) was collected in one 260 ml fraction.

The bound proteins were subsequently released from the column (eluted) by applying the following buffers:
- 10 mM sodium citrate pH 6.0 (conductivity of the buffer: 2.32 mS/cm). The flow through (eluted proteins, eluate) was collected in one fraction 192 ml resulting conductivity in eluate=2.0 mS/cm.
- 10 mM NaOH (conductivity of the buffer: 2.4 mS/cm). The flow through (eluted proteins, eluate) was collected in one fraction 140 ml resulting conductivity in eluate=1.0 mS/cm. The resulting pH in the eluate was pH 7.59 because the proteins were released with a dilute sodium hydroxide buffer.
- The performance of the adsorbent was determined by SDS-PAGE (as described in EXAMPLE 3). See FIG. 17.
- Dry matter determinations were performed on eluate 1 and eluate 2 (as described in EXAMPLE 3)

The protein concentration in eluate 1 was 3.2 mg/ml resulting in a yield of 1.0 mg protein per ml soy bean extract loaded onto the column.

The protein concentration in eluate 2 was 6.2 mg/ml resulting in a yield of 1.4 mg protein per ml soy bean extract loaded onto the column.

This results in a total adsorbent binding capacity of 36 mg protein per ml adsorbent. The results indicate that the trypsin inhibitor is selectively eluted (at pH 6.0, see lane 7) from the adsorbent with the 4-aminobenzoic acid ligand before the other proteins which were eluted by the 10 mM NaOH solution (see lane 8).

Lane 1=soy extract at pH 4.5
Lane 2=Flow through fraction 1 (non-bound proteins) from load of adsorbent with the ligand 4-aminobenzoic acid (4% agarose beads) at pH 4.5.
Lane 3=Flow through fraction 2 (non-bound proteins) from load of adsorbent with the ligand 4-aminobenzoic acid (4% agarose beads) at pH 4.5.
Lane 4=Flow through fraction 3 (non-bound proteins) from load of adsorbent with the ligand 4-aminobenzoic acid (4% agarose beads) at pH 4.5.
Lane 5=Flow through pool of fraction 1 to 3 (non-bound proteins) from load of adsorbent with the ligand 4-aminobenzoic acid (4% agarose beads) at pH 4.5.
Lane 6=Wash (non-bound and loosely bound proteins) of the adsorbent with the ligand 4-aminobenzoic acid (4% agarose beads)
Lane 7=Eluate (Bound and subsequently released proteins) from adsorbent with the ligand 4-aminobenzoic acid (4% agarose beads) at pH 6.0
Lane 8=Eluate (Bound and subsequently released proteins) from adsorbent with the ligand 4-aminobenzoic acid (4% agarose beads) with 10 mM NaOH Example 22

The example shows how the trypsin inhibitor can be removed from precipitated soy proteins.

Soy extract (produced at neutral pH according to EXAMPLE 2) was centrifuged at 10,000 RPM to remove non-soluble and precipitated material, 20 ml of the centrifuged extract was pH-adjusted with 1 M HCl to pH 4.5. The extract was centrifuged at 10,000 RPM. The supernatant was collected. The pellet was re-solubilized in 20 ml 10 mM di-potassium hydrogenphosphate pH 8.0. The trypsin inhibitor in the resolubilized soy proteins was selectively bound to an adsorbent coupled with the ligand benzylamine (Produced as described in EXAMPLE 1) (the ligand concentration was determined with titration to be 55 mmol/L adsorbent) at pH 8.0.

Procedure

Column preparation and flow rate as per Example 4. After packing the adsorbent was equilibrated with 10 ml 10 mM tris pH 8.0. The re-solubilized soy protein solution was pH-adjusted with 1 M NaOH to pH 8.0. The solution was centrifuged at 10,000 RPM to remove non-soluble and precipitated material. 14 ml was loaded onto the column. The flow through (non-bound proteins) was collected in four 3.5 ml fractions. The adsorbent was washed with 5 ml of deionized water. The flow through (non-bound and loosely bound proteins) was collected in one 5 ml fraction.

The bound proteins were subsequently released from the column (eluted) by applying 10 ml 10 mM NaOH. The flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIG. 18.

The results indicate that when pH is adjusted to pH 4.5 most of the soy bean proteins are precipitated (lane 1 represents all the protein bands in the soy extract at pH 6.0, lane 2 represents the supernatant when the soy proteins have been precipitated at pH 4.5, significant bands are not represented due to precipitation)

The proteins in the pellet (from the pH 4.5 precipitation) can be re-solubilized in a phosphate buffer pH 8.0. (Lane 3 represents the re-solubilized proteins where the significant protein bands appear again).

The re-solubilized protein fraction contains trypsin inhibitor (see lane 3). The adsorbent coupled with the ligand benzylamine selectively binds essentially all the trypsin inhibitor applied to the column and the other proteins in this fraction is recovered in the flow through from this adsorbent (see lane 4 to 8 representing the run-through fractions containing non-bound proteins=all major protein bands in the re-solubilized protein fraction except the trypsin inhibitor which is practically absent from these fractions). The trypsin inhibitor is recovered in the eluate from the experiment (see lane 10)

Lane 1=soy extract at pH 6.0
Lane 2=Supernatant after precipitation of the soy proteins at pH 4.5
Lane 3=Re-solubilized pellet pH 8.0 (from the precipitation of soy protein at pH 4.5)
Lane 4=Flow through fraction 1 (non-bound proteins) from load of adsorbent with the ligand Benzylamine at pH 8.0.
Lane 5=Flow through fraction 2 (non-bound proteins) from load of adsorbent with the ligand Benzylamine at pH 8.0.
Lane 6=Flow through fraction 3 (non-bound proteins) from load of adsorbent with the ligand Benzylamine at pH 8.0.
Lane 7=Flow through fraction 4 (non-bound proteins) from load of adsorbent with the ligand Benzylamine at pH 8.0.
Lane 8=Flow through pool of fraction 1 to 4 (non-bound proteins) from load of adsorbent with the ligand Benzylamine at pH 8.0.
Lane 9=Wash (non-bound and loosely bound proteins) of the adsorbent with the ligand Benzylamine
Lane 10=Eluate (Bound and subsequently released proteins) from adsorbent with the ligand Benzylamine Example 23

The example shows how the soy bean proteins precipitate at pH 4.5 when the trypsin inhibitor was present and when the trypsin inhibitor has been depleted before precipitation at pH 4.5. The trypsin inhibitor was selectively bound to an adsorbent coupled with the ligand benzylamine (the ligand concentration was determined with titration to be 55 mmol/L adsorbent) at pH 8.0.

The flow through from this experiment (still containing a small amount of trypsin inhibitor) was pH adjusted to pH 7.0 and the small amount of remaining trypsin inhibitor was selectively bound to an adsorbent coupled with the ligand benzylamine (the ligand concentration was determined with titration to be 55 mmol/L adsorbent) at pH 7.0.

The experiments were performed with Expanded Bed Adsorption (EBA) chromatography. EBA column used for the experiment: 1 cm diameter laboratory EBA column with a 150 cm glass tube (Cat. No.: 7010-0100+7010-1500, Upfront Chromatography A/S, Denmark)

Procedure Column 1 (Load pH=8.0)

The column was packed with 50 cm settled bed height, equal to 40 ml adsorbent. Flow rate during the entire experiment: 10 cm/min=8 ml/min. After packing the adsorbent was equilibrated with 200 ml 10 mM tris pH 8.0. The soy extract (produced at pH 9 according to EXAMPLE 2) was pH-adjusted with 1 M HCl to pH 8.0. The extract was loaded directly onto the column without centrifugation. 300 ml of the extract was loaded onto the column. The flow through (non-bound proteins) was collected in one 300 ml fraction. The adsorbent was washed with 280 ml of deionized water. The flow through (non-bound and loosely bound proteins) was collected in one 245 ml fraction.

The bound proteins were subsequently released from the column (eluted) by applying the following buffer:

10 mM NaOH (conductivity of the buffer: 2.4 mS/cm). The flow through (eluted proteins, eluate) was collected in one fraction 325 ml resulting conductivity in eluate=606 µS/cm.

Procedure Column 2 (Load pH=7.0)

The column was packed with 50 cm settled bed height, equal to 40 ml adsorbent. Flow rate during the entire experiment: 10 cm/min=8 ml/min. After packing the adsorbent was equilibrated with 200 ml 10 mM sodium citrate pH 6.0. The soy extract (=flow through from load of column 1 described above) was pH-adjusted with 1 M HCl to pH 7.0. The extract was loaded directly onto the column without centrifugation. 200 ml of the extract was loaded onto the column. The flow through (non-bound proteins) was collected in one 200 ml fraction. The adsorbent was washed with 300 ml of deionized water. The flow through (non-bound and loosely bound proteins) was collected in one 285 ml fraction.

The bound proteins were subsequently released from the column (eluted) by applying the following buffer:

10 mM NaOH (conductivity of the buffer: 2.4 mS/cm). The flow through (eluted proteins, eluate) was collected in one fraction 275 ml. Resulting conductivity in eluate=702 µS/cm.

Procedure, Precipitation of Soy Proteins

Soy extract produced at pH 9.0 (according to EXAMPLE 2), the soy extract depleted from most trypsin inhibitor (at pH 8.0) and the soy extract totally depleted from trypsin inhibitor at pH 7.0 have been pH-adjusted to pH 4.5 with 1 M hydrogen chloric acid. The preparations were centrifuged at 10,000 rpm to remove non-soluble and precipitated material and the supernatants were tested with SDS-PAGE according to EXAMPLE 3. See FIG. 19a-c.

The performance of the adsorbent at the different load pH-values was determined by SDS-PAGE (as described in EXAMPLE 3). See FIG. 19a-c.

Dry matter determinations were performed on the two eluates (as described in EXAMPLE 3)

The protein concentration in the eluate from column 1 was 3.08 mg/ml resulting in a yield of 3.33 mg protein per ml soy bean extract loaded onto the column.

The protein concentration in the eluate from column 2 was 4 mg/ml resulting in a yield of 5.5 mg protein per ml soy bean extract loaded onto the column.

The results indicate that the adsorbent bound main fraction of the trypsin inhibitor applied to column 1 at pH 8.0 (see lane 2 representing the run-through fraction containing non-bound proteins is practically devoid of the trypsin inhibitor band). The eluate contains the trypsin inhibitor and a very minor fraction of the other proteins (see lane 4).

The results indicate that the adsorbent bound main fraction of the trypsin inhibitor applied to column 2 at pH7.0 (see lane 6 representing the run-through fraction containing non-bound proteins is devoid of the trypsin inhibitor band). The eluate contains the trypsin inhibitor and a fraction of the other proteins (see lane 8).

From the SDS-PAGE it was concluded that when the trypsin inhibitor was totally depleted from the extract then the soy bean lectin and soy bean lipoxidase precipitates better (see lane 12. The band representing lipoxidase is not there meaning that the protein is precipitated, the band is still present in lane 10 and 11 where the trypsin inhibitor also is present. The band representing the lectin is very weak compared to lane 10 and 11 meaning that more lectin has been precipitated).

Lane 1=soy extract at pH 8.0
Lane 2=Flow through fraction (non-bound proteins) from load of adsorbent with the ligand benzylamine at pH 8.0 (column 1).
Lane 3=Wash (non-bound and loosely bound proteins) of the adsorbent with the ligand benzylamine
Lane 4=Eluate (Bound and subsequently released proteins) from adsorbent with the ligand benzylamine Lane 5=soy extract flow through from load of column 1 at pH 7.0

Lane 6=Flow through fraction (non-bound proteins) from load of adsorbent with the ligand benzylamine at pH 7.0 (column 2).

Lane 7=Wash (non-bound and loosely bound proteins) of the adsorbent with the ligand benzylamine Lane 8=Eluate (Bound and subsequently released proteins) from adsorbent with the ligand benzylamine Lane 10=Supernatant from soy extract produced at pH 9.0 pH adjusted to pH 4.5 with 1 M hydrogen chloric acid Lane 11=Supernatant from the soy extract depleted from trypsin inhibitor (at pH 8.0) pH adjusted to pH 4.5 with 1 M hydrogen chloric acid Lane 12=Supernatant from the soy extract totally depleted from trypsin inhibitor at pH 7.0 pH-adjusted to pH 4.5 with 1 M hydrogen chloric acid.

Example 24

This example shows how an enzymatic assay determines that the trypsin inhibitor is removed from a soy bean extract.

A specific amount of trypsin (from bovine pancreas, T4665, Sigma, USA) is added to the soy bean extract. The same amount of trypsin is also added to the flow-through fraction from the loading of soy extract to the adsorbent coupled with the ligand benzylamine at pH 6.0. This fraction has a very low content of trypsin inhibitor (the trypsin inhibitor binds to the benzylamine ligand). The trypsin/soy extract solution is mixed with the substrate N-benzoyl-L-arginin-4-nitroanilid, hydrochloride (B3279, Sigma, USA).

The breakdown product of the substrate creates a yellow colour which can be measured at 410 nm. The development of colour is measured over time (two minutes) and ΔAbs is calculated. The higher ΔAbs, the higher trypsin activity in the sample. When the trypsin inhibitor is present in the trypsin/soy extract solution and mixed with the substrate then ΔAbs is low because the trypsin inhibitor inhibits the trypsin substrate reaction. Vice versa, when the trypsin inhibitor is not present the ΔAbs is high because there is nothing to inhibit the trypsin substrate reaction.

The following procedure has been used:

Substrate solution: 1.5 mM N-benzoyl-L-arginin-4-nitroanilid, hydrochloride in 0.1 M tris, 10 mM calcium chloride pH 8.0.

Trypsin solution: 0.3 mg trypsin/ml in 1 mM HCl.

Dilution of soy extract: The soy extract is centrifuged at 10,000 rpm and the supernatant is diluted in 1 mM HCl. 100 µl of diluted soy extract is mixed with 50 µl trypsin solution for 20 min. After 20 min. 600 µl 0.1 M tris, 10 mM calcium chloride pH 8.0 is added. 375 µl substrate solution is added. The sample is mixed well and immediately measured at 410 nm for 2 minutes with a spectrophotometer.

The following samples have been measured:

a) The trypsin activity alone with no soy extract present b) Soy extract at pH 6 c) Soy extract where the trypsin inhibitor has been removed with the adsorbent coupled with the ligand Benzylamine at pH 6.0 (the procedure described in EXAMPLE 14 has been used to produce this sample).

The table shows the results (ΔAbs) for each of the above mentioned samples.

| Sample | Dilution of soy sample | ΔAbs |
|---|---|---|
| a) The trypsin activity alone with no soy extract present | No soy added, 100 µl of water is added instead of extract | 0.2339 |
| b) Soy extract at pH 6 | 40x | 0.0390 |
| c) Soy extract where the trypsin inhibitor has been removed | 40x | 0.2031 |

The numbers show that when the non-treated soy extract (containing the trypsin inhibitor) is added to the trypsin, the ΔAbs decreases with a factor of six, meaning that the trypsin inhibitor inhibits the reaction between the trypsin and the substrate (less yellow colour is developed). When the trypsin is mixed with the soy extract where most of the trypsin inhibitor has been removed by the adsorbent coupled with the ligand Benzylamine at pH 6.0, then the ΔAbs is almost the same as if no trypsin inhibitor is present, meaning that the adsorbent has bound most (>90%) of the trypsin inhibitor.

The invention claimed is:

1. A process for the separation of soy protein, said process comprising the steps of:
    i. providing an aqueous extract of soy protein or a solution of soy protein, said extract or solution of soy protein comprising at least two types of soy proteins;
    ii. passing said aqueous extract or solution of soy protein through at least one expanded bed absorption process, wherein said expanded bed absorption process comprises contacting said aqueous extract or solution of soy protein with at least one adsorbent resin which selectively adsorbs at least a first type of soy protein to provide a non-bound protein fraction and a bound protein fraction, said adsorbent resin comprising:
        at least one ligand (L1), said at least one ligand (L1) comprising an aromatic or heteroaromatic ring system and one or more acidic groups, or
        at least one ligand (L2), said at least one ligand (L2) comprising an alkylamine or alkylarylamine, wherein said alkylamine or alkylarylamine moieties in ligands (L2) comprise an amine substituted with one or more groups selected from:
            a. an aryl, benzyl or heteroaryl group;
            b. an alkyl group having 4-16 carbon atoms which may be straight, branched or cyclic;
        or combinations thereof;
    iii. isolating said first type of soy protein from said adsorbent resin, by elution of the non-bound protein fraction; and
    iv. isolating the second type of soy protein from said adsorbent resin to provide a second soy protein composition which is depleted in said first type of soy protein.

2. The process according to claim 1, further comprising the step of denaturing the second soy protein composition to provide a denatured second soy protein composition.

3. The process according to claim 1, wherein the first type of protein is beta-conglycinin.

4. The process according to claim 1, wherein the first type of protein is trypsin inhibitor (TI) protein.

5. The process according to claim 4, further comprising the step of denaturing the isolated trypsin inhibitor (TI) protein to provide denatured TI protein.

6. The process according to claim 5, further comprising the step of combining said denatured TI protein with the second soy protein composition obtained in step (iv) to provide a first combined soy protein product.

7. The process according to claim 5, further comprising the step of combining said denatured TI protein with the denatured second soy protein composition obtained in claim 2 to provide a second combined soy protein product.

8. The process according to claim 6, wherein said first combined soy protein product is denatured, to form a third combined soy protein product.

9. The process according to claim 1, wherein the ligands (L1) comprise an aromatic ring system.

10. The process according to claim 1, wherein said alkylamine or alkylarylamine moieties in ligands (L2) comprise an amine substituted with one or more groups selected from: an alkyl group having 4-16 carbon atoms which may be straight, branched or cyclic.

11. The process according to claim 10, wherein said ligands (L2) are selected from butylamine, hexylamine, octylamine di-butylamine, pentylamine, n-pentylamine, N,N-di-methyl-1,3-di-aminopropane, 1,3-diaminopropane, 1,6-diamino hexane, 1,6-diamino hexane, 1,8-aminooctane, 1,9-di-aminononane, 1,12-aminododecane, 2-aminobenzylamine, 2-aminobenzimidazole, 2-aminoimidazole, 2,4-di-amino-6-hydroxypyrimidine or benzylamine.

12. The process according to claim 1, wherein elution takes place at a pH of 7.0 or more.

13. A second soy protein composition, depleted in said first type of soy protein, obtained by the process of claim 12.

14. A denatured second soy protein composition, obtained by the process of claim 2.

15. A first combined soy protein product, obtained by the process of claim 6.

16. A second combined soy protein product, obtained by the process of claim 7.

17. A third combined soy protein product, obtained by the process of claim 8.

18. The process according to claim 9, wherein the aromatic ring system comprises a phenyl or naphthyl radical.

* * * * *